United States Patent
Gutierrez et al.

(10) Patent No.: US 12,269,880 B2
(45) Date of Patent: Apr. 8, 2025

(54) LAG3 BINDING PEPTIDES

(71) Applicant: Leidos, Inc., Reston, VA (US)

(72) Inventors: Gabriel M. Gutierrez, Reston, VA (US); Vinayaka Kotraiah, Reston, VA (US); Timothy W. Phares, Reston, VA (US); James Pannucci, Reston, VA (US); Marc Mansour, Reston, VA (US)

(73) Assignee: Leidos, Inc., Reston, VA (US)

( * ) Notice: Subject to any disclaimer, the term of this patent is extended or adjusted under 35 U.S.C. 154(b) by 0 days.

(21) Appl. No.: 17/854,227

(22) Filed: Jun. 30, 2022

(65) Prior Publication Data

US 2022/0395554 A1 Dec. 15, 2022

Related U.S. Application Data

(62) Division of application No. 16/879,884, filed on May 21, 2020, now Pat. No. 11,407,829.

(60) Provisional application No. 62/851,142, filed on May 22, 2019.

(51) Int. Cl.
| | |
|---|---|
| C07K 7/08 | (2006.01) |
| A61K 38/04 | (2006.01) |
| A61K 38/10 | (2006.01) |
| A61K 38/16 | (2006.01) |
| A61K 39/395 | (2006.01) |
| A61K 45/06 | (2006.01) |
| C07K 14/00 | (2006.01) |
| C07K 16/28 | (2006.01) |
| C12N 15/11 | (2006.01) |

(52) U.S. Cl.
CPC .......... *C07K 16/2803* (2013.01); *A61K 38/04* (2013.01); *A61K 38/10* (2013.01); *A61K 38/16* (2013.01); *A61K 39/3955* (2013.01); *A61K 45/06* (2013.01); *C07K 7/08* (2013.01); *C07K 14/00* (2013.01); *C12N 15/11* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| 9,073,990 | B2 | 7/2015 | Paas et al. |
| 11,338,040 | B2 | 5/2022 | Gutierrez et al. |

FOREIGN PATENT DOCUMENTS

| CN | 105504018 A | 4/2016 |
| WO | 2016028672 A1 | 2/2016 |
| WO | 2017062888 A1 | 4/2017 |
| WO | 2018006005 A1 | 1/2018 |
| WO | 2018039147 A1 | 3/2018 |
| WO | 2018167320 A1 | 9/2018 |
| WO | 2020237050 A1 | 11/2020 |

OTHER PUBLICATIONS

Murciano-Goroff et al., "The future of cancer immunotherapy: microenvironment-targeting combinations," Cell Research 30, 507-19, 2020.
Yayi et al., "Lymphocyte-activation gene-3, an important immune checkpoint in cancer", Cancer Science, vol. 107, No. 9, Aug. 25, 2016, pp. 1193-1197.
Andrews et al., "LAG3 (CD223) as a Cancer Immunotherapy Target," Immunol. Rev. 276, 80-96, 2017.
English translation of CN10550418.
Gutierrez et al., U.S. Appl. No. 17/337,489, filed Jun. 3, 2021.
Gutierrez et al., U.S. Appl. No. 17/386,637, filed Jul. 28, 2021.
Lichtenegger et al., "Targeting LAG-3 and PD-1 to Enhance T Cell Activation by Antigen-Presenting Cells," Frontiers in Immunology 9, Article 385, Feb. 2018.
Mao et al., "Pathological ?-synuclein transmittion initiated by binding lymphocyte-activation gene 3," Science 353, Sep. 2016.
Patil et al., "Targeting Immune Cell Checkpoints during Sepsis," Int. J. Mol. Sci. 18, 24 pages, 2017.
Wang et al., "Fibrinogen-like Protein 1 is a Major Immune Inhibitory Ligand of LAG-3," Cell 176, 334-47, Jan. 10, 2019.
Anonymous, "PEP-CTERM sorting domain-containing protein [Akkermansia muciniphila]—Protein—NCBI," XP055858840, retrieved from the internet on Aug. 11, 2021 at URL:https://www.ncbi.nlm.nih.gov/protein/WO_102748186, Jun. 1, 2019.
Gutierrez et al., U.S. Appl. No. 17/337,489, filed Jun. 3, 2021, Allowed Claims as filed in Preliminary Amendment filed Jun. 28, 2021, 4 pages.
Gutierrez et al., U.S. Appl. No. 17/337,489, filed Jun. 3, 2021, Notice of Allowance dated Mar. 28, 2022, 11 pages.
Gutierrez et al., U.S. Appl. No. 17/386,637, filed Jul. 28, 2021, Preliminary Amendment filed Jul. 28, 2021, 5 pages.
Gutierrez et al., U.S. Appl. No. 17/337,489, filed Jun. 3, 2021, Preliminary Amendment filed Jun. 28, 2021, 6 pages.
Gutierrez et al., U.S. Appl. No. 17/337,489, filed Jun. 3, 2021, Response to Restriction Requirement filed Mar. 3, 2022, 1 page.
Gutierrez et al., U.S. Appl. No. 17/337,489, filed Jun. 3, 2021, Restriction Requirement dated Jan. 6, 2022, 8 pages.
Gutierrez et al., U.S. Appl. No. 16/879,884, filed May 21, 2020, Final Office Action dated Nov. 30, 2021, 13 pages.

(Continued)

*Primary Examiner* — Zachary S Skelding
(74) *Attorney, Agent, or Firm* — Banner & Witcoff, Ltd.

(57) ABSTRACT

This disclosure provides nucleic acids encoding peptides which bind to LAG3 and can be used to block the interaction of LAG 3 with other molecules such as MHC-II, FGL1, and α-synuclein. These peptides can be used for various therapeutic purposes, such as inhibiting the progression of a hyperproliferative disorder, including cancer, or inhibiting the progression of a synucleinopathy, inhibiting the progression of sepsis, inhibiting the progression of an infectious disease, and enhancing a response to a vaccine.

12 Claims, 15 Drawing Sheets

Specification includes a Sequence Listing.

(56) References Cited

OTHER PUBLICATIONS

Gutierrez et al., U.S. Appl. No. 16/879,884, filed May 21, 2020, Nonfinal Office Action dated Jul. 21, 2021, 18 pages.
Gutierrez et al., U.S. Appl. No. 16/879,884, filed May 21, 2020, Reponse to Restriction Requirement filed Jun. 15, 2021, 6 pages.
Gutierrez et al., U.S. Appl. No. 16/879,884, filed May 21, 2020, Response to Final Office Action filed Feb. 28, 2022, 5 pages.
Gutierrez et al., U.S. Appl. No. 16/879,884, filed May 21, 2020, Response to Nonfinal Office Action filed Oct. 21, 2021, 8 pages.
Gutierrez et al., U.S. Appl. No. 16/879,884, filed May 21, 2020, Restriction Requirement dated May 17, 2021, 6 pages.
Gutierrez et al., International Patent Application No. PCT/US2020/03996 filed May 21, 2020, International Search Report and Written Opinion of the International Searching Authority dated Sep. 17, 2020, 18 pages.
Gutierrez et al., International Patent Application No. PCT/US2020/03996 filed May 21, 2020 International Search Report of the International Searching Authority and Invitation to Pay Additional Fees dated Jul. 27, 2020, 14 pages.
Anonymous, "PEP-CTERM sorting domain-containing protein [Akkermansia muciniphila]—Protein—NCBI," XP055858840, URL:https://www.ncbi.nlm.nih.gov/protein/WO_102748186, Jun. 1, 2019.

SEQUENCE LISTING

```
<160> NUMBER OF SEQ ID NOS: 9

<210> SEQ ID NO 1
<211> LENGTH: 20
<212> TYPE: PRT
<213> ORGANISM: Artificial Sequence
<220> FEATURE:
<223> OTHER INFORMATION: LAG3-11 peptide

<400> SEQUENCE: 1

Ser Ala Pro Trp Glu Pro Leu His Trp Pro Glu Asp Trp Trp Gln Gly
1               5                   10                  15

Thr Gly Glu Trp
            20

<210> SEQ ID NO 2
<211> LENGTH: 20
<212> TYPE: PRT
<213> ORGANISM: Artificial Sequence
<220> FEATURE:
<223> OTHER INFORMATION: LAG3-42 peptide

<400> SEQUENCE: 2

Asp Trp Asn Phe Gln Gln Trp Asp Trp Lys Lys His Asn His Leu Asp
1               5                   10                  15

Ser His Val Val
            20

<210> SEQ ID NO 3
<211> LENGTH: 20
<212> TYPE: PRT
<213> ORGANISM: Artificial Sequence
<220> FEATURE:
<223> OTHER INFORMATION: LAG3-48 peptide
```

-continued

```
<400> SEQUENCE: 3

Phe Tyr Ser Pro Asn His Glu Glu Tyr His Asp Trp Asn Val Asp Ser
1               5                   10                  15

Ser Val Asn Glu
            20

<210> SEQ ID NO 4
<211> LENGTH: 20
<212> TYPE: PRT
<213> ORGANISM: Artificial Sequence
<220> FEATURE:
<223> OTHER INFORMATION: LAG3-51 peptide

<400> SEQUENCE: 4

Lys Val Trp Gln Val Pro Gln Asp Thr Gln His Trp Leu Ser Pro Asn
1               5                   10                  15

Phe Tyr Ser Val
            20

<210> SEQ ID NO 5
<211> LENGTH: 13
<212> TYPE: PRT
<213> ORGANISM: Artificial Sequence
<220> FEATURE:
<223> OTHER INFORMATION: LAG3-54 peptide

<400> SEQUENCE: 5

Ala Cys Gly Pro Gly Ser Phe Gly Asp Cys Gly Gly Gly
1               5                   10

<210> SEQ ID NO 6
<211> LENGTH: 21
<212> TYPE: PRT
<213> ORGANISM: Artificial Sequence
<220> FEATURE:
<223> OTHER INFORMATION: LAG3-56 peptide

<400> SEQUENCE: 6

His Ile Gln Asn Trp Ser Tyr Trp Leu Asn Gln Asp Met Met Asn Gln
1               5                   10                  15

Gln Val Trp Lys Ser
            20

<210> SEQ ID NO 7
<211> LENGTH: 18
<212> TYPE: PRT
<213> ORGANISM: Artificial Sequence
<220> FEATURE:
<223> OTHER INFORMATION: LAG3-60 peptide

<400> SEQUENCE: 7

His Glu Ser Gly Ser Val Pro His Pro Trp Gln Phe Phe Thr His Tyr
1               5                   10                  15

Val Ser

<210> SEQ ID NO 8
<211> LENGTH: 17
<212> TYPE: PRT
<213> ORGANISM: Gallus gallus

<400> SEQUENCE: 8

Ile Ser Gln Ala Val His Ala Ala His Ala Glu Ile Asn Glu Ala Gly
1               5                   10                  15
```

Arg

<210> SEQ ID NO 9
<211> LENGTH: 20
<212> TYPE: PRT
<213> ORGANISM: Artificial Sequence
<220> FEATURE:
<223> OTHER INFORMATION: negative control peptide

<400> SEQUENCE: 9

```
Ser Ser Tyr His His Phe Lys Met Pro Glu Leu His Phe Gly Lys Asn
1               5                   10                  15

Thr Phe His Gln
            20
```

LAG3 BINDING PEPTIDES

This application is a division of Ser. No. 16/879,884 filed on May 21, 2020, which claims priority to Ser. No. 62/851,142 filed on May 22, 2019.

This application incorporates by reference the contents of a 2,469 byte text file created on Feb. 25, 2022 and named "substitutesequencelisting.txt," which is the sequence listing for this application.

Each scientific reference, patent, and published patent application cited in this disclosure is incorporated herein by reference in its entirety.

TECHNICAL FIELD

This disclosure relates generally to immunomodulatory peptides.

BACKGROUND

Lymphocyte activation gene 3 (LAG3, also known as LAG-3, LAG 3, Lag3, CD223, FDC protein) is a member of the immunoglobulin superfamily of receptors.

LAG3 is expressed on immune cells (activated T cells, Huard et al., 1994; natural killer cells, Triebel et al., 1990; B cells, Kisielow et al., 2005; plasmacytoid dendritic cells, Workman et al., 2009), where it binds to MHC class II (MHC-II) and serves as an immune checkpoint receptor. LAG3 also binds to fibrinogen-like protein (FGL1), and disrupting this binding can potentiate anti-tumor immunity (Wang et al., 2019). There is a continuing need for useful modulators of immune checkpoint pathways.

LAG3 is also expressed on neurons, where it serves as a receptor for the α-synuclein aggregates characteristic of synucleinopathies (Mao et al., 2016). Synucleinopathies are disorders characterized by the abnormal accumulation of aggregates of α-synuclein protein in neurons, nerve fibers, or glial cells. Synucleinopathies include idiopathic and inherited forms of Parkinson's disease (PD); diffuse Lewy body (DLB) disease, also known as dementia with Lewy bodies or Lewy body dementia; incidental Lewy body disease; Lewy body variant of Alzheimer's disease (LBV); combined Alzheimer's and Parkinson disease (CAPD); pure autonomic failure (PAF); multiple system atrophy (MSA), such as olivopontocerebellar atrophy, striatonigral degeneration, and Shy-Drager Syndrome; pantothenate kinase-associated neurodegeneration; Down's Syndrome; Gaucher disease-related synucleinopathies; and neurodegeneration with brain iron accumulation. There is a continuing need for therapeutic agents for treating or managing symptoms of synucleinopathies.

DETAILED DESCRIPTION

Figure 1A:
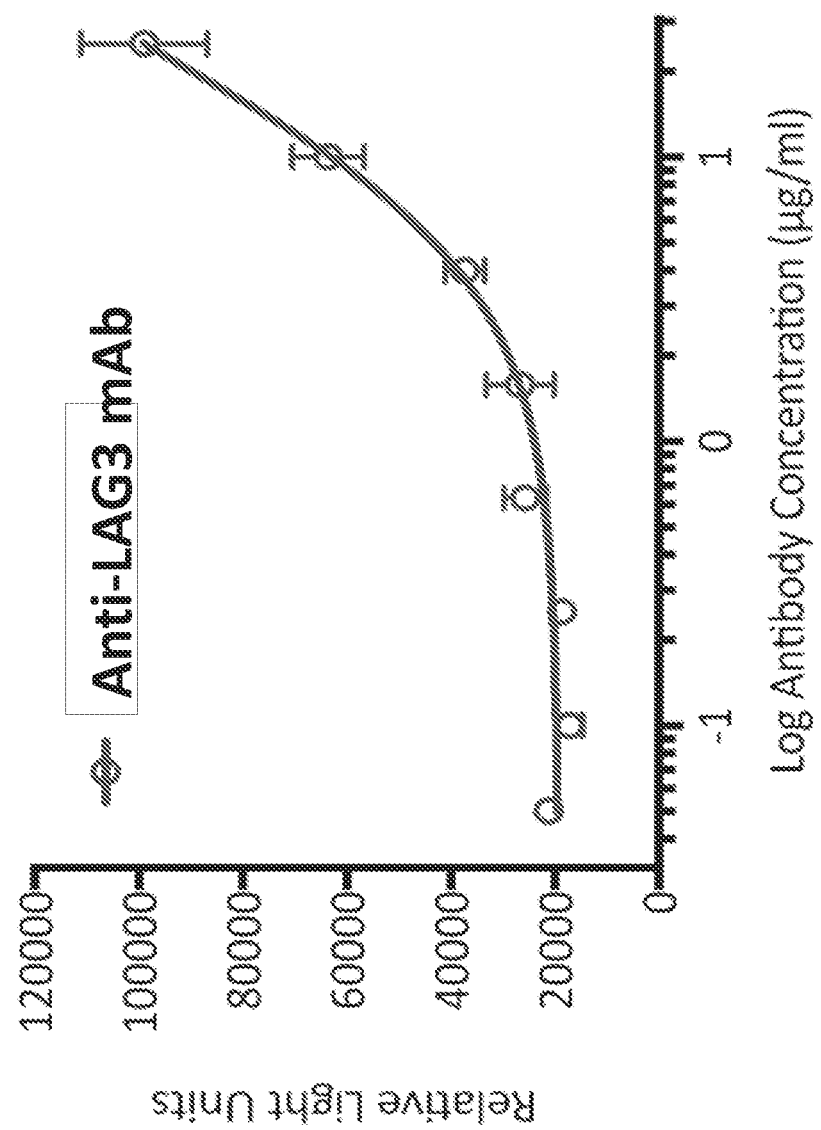
FIG. 1A and FIG. 1B are graphs showing the results of LAG3 blockage functional inhibition assays described in Example 2.

This disclosure provides peptides that bind to LAG3 and can be used to block its interaction with other molecules such as MHC-II, FGL1, and α-synuclein.

TABLE 1

| peptide | amino acid sequence | SEQ ID NO: |
|---|---|---|
| LAG3-11 | SAPWEPLHWPEDWWQGTGEW | 1 |
| LAG3-42 | DWNFQQWDWKKHNHLDSHVV | 2 |
| LAG3-48 | FYSPNHEEYHDWNVDSSVNE | 3 |
| LAG3-51 | KVWQVPQDTQHWLSPNFYSV | 4 |
| LAG3-54 | ACGPGSFGDCGGG | 5 |
| LAG3-56 | HIQNWSYWLNQDMMNQQVWKS | 6 |
| LAG3-60 | HESGSVPHPWQFFTHYVS | 7 |

In some embodiments, a disclosed peptide is modified using chemical or recombinant methods to enhance its stability or other pharmacokinetic properties. See, e.g., US 2017/0020956. Modifications include, but are not limited to, replacement of one or more L-amino acid with its corresponding D-form, acetylation on a C- and/or N-terminal residue, amidation on a C- and/or N-terminal residue, cyclization, esterification, glycosylation, acylation, attachment of myristic or palmitic acid, addition of an N-terminal glycine, addition of lipophilic moieties such as long fatty acid chains, and PEGylation.

Peptides can be made by any method known in the art, including synthetic methods, recombinant methods, or both. Synthetic methods include solid-phase and solution methods, and may include the use of protective groups. See, e.g., Bodanszky et al. (1976), McOmie (1973), Merrifield (1963), Neurath et al. (1976), Stuart & Young (1984).

Recombinant production of peptides can be carried out using any nucleotide sequence(s) encoding the peptides in any suitable expression system. Nucleic acid molecules encoding one or more of the disclosed peptides can be incorporated into an expression cassette that includes control elements operably linked to the coding sequences. Control elements include, but are not limited to, initiators, promoters (including inducible, repressible, and constitutive promoters), enhancers, and polyadenylation signals. Signal sequences can be included. The expression cassette can be provided in a vector that can be introduced into an appropriate host cell for production of the peptide(s). Methods of constructing expression cassettes and expression vectors are well known. Expression vectors can include one or more expression cassettes encoding one or more peptides comprising, consisting essentially or, or consisting of any of SEQ ID NOS:1-7.

In some embodiments, one or more peptides are expressed as a component of a fusion protein. Other components of the fusion protein can be, for example, a cytokine or an engineered T cell receptor (TCR). A fusion protein can comprise one or more linkers between its components. In some embodiments, a linker between a peptide and another component of the fusion protein can comprise a proteolytic cleavage site to release the peptide after expression of the fusion protein. See, e.g., US 2016/0138066; US 2018/0135060; US 2014/0343251; US 2012/0142891; Rodriguez et al., 2014.

In some embodiments, a component of a fusion protein is a moiety, such as albumin or transthyretin, which can enhance the plasma half-life of the peptide. In other embodiments, a peptide or a modified version of a peptide is conjugated to the moiety. Methods of preparing such conjugates are well known in the art (e.g., Penchala et al., 2015; Kontermann, 2016; Zorzi et al., 2017).

In some embodiments, a component of a fusion protein is a partner molecule, such as a peptide or protein such as an antibody intended to increase the half-life of a peptide or modified peptide in vivo and/or to provide specific delivery to a target tissue or cell. Alternatively, a peptide or modified version thereof can be conjugated to the partner molecule. Conjugation may be direct or can be via a linker. In some of these embodiments, a peptide or a modified version thereof can be altered to substitute one or more amino acids with amino acids used to attach partner molecules, such as lysine, or by N-terminal extension of the peptide with, e.g., 1, 2, 3, or 4 glycine spacer molecules.

This disclosure also provides CAR-T cells that express one or more of the disclosed peptides. Methods of preparing CAR-T cells are disclosed, for example, in U.S. Pat. Nos. 9,328,156; 9,845,362; and 9,101,584.

This disclosure also provides oncolytic viruses containing a nucleic acid molecule encoding one or more of the disclosed peptides. See US 2017/0157188; Lawler et al., 2017; US 2015/0250837. Oncolytic viruses include, but are not limited to, reovirus, Seneca Valley virus, vesicular stomatitis virus, Newcastle disease virus, herpes simplex virus, morbillivirus virus, retrovirus, influenza virus, Sindbis virus, poxvirus, and adenovirus.

Examples of oncolytic reovirus include REOLYSIN® (pelareorep) and reoviruses disclosed in US 2017/0049829.

Examples of oncolytic Seneca Valley virus include NTX-101 (Rudin et al., 2011).

Examples of oncolytic vesicular stomatitis virus are disclosed in Stojdl et al., 2000; and Stojdl et al., 2003.

Examples of oncolytic Newcastle disease virus include 73-T PV701 and HDV-HUJ strains (see also Phuangsab et al., 2001; Lorence et al., 2007; and Freeman et al., 2006).

Examples of oncolytic herpes simplex virus include NV1020 (Geevarghese et al., 2010) and T-VEC (Andtbacka et al., 2013).

Examples of oncolytic morbillivirus virus include oncolytic measles viruses such as MV-Edm (McDonald et al., 2006) and HMWMAA (Kaufmann et al., 2013).

Examples of oncolytic retrovirus are disclosed in Lu et al., 2012.

Examples of oncolytic influenza virus are disclosed, for example, in US 2018/0057594.

Examples of oncolytic Sindbis virus are disclosed, for example, in Lundstrom, 2017.

Examples of oncolytic poxvirus are disclosed, for example, in Chan & McFadden, 2014.

Examples of oncolytic adenovirus include ONYX-015 (Khuri et al., 2000) and H101 or Oncorine (Liang, 2018).

Therapeutic Uses

The peptides and modified versions thereof disclosed herein have a number of therapeutic applications, including treating hyperproliferative disorders (e.g., cancer). "Treat," as used herein, includes reducing or inhibiting the progression of one or more symptoms of the condition for which a peptide or modified version thereof is administered. The peptides and modified versions thereof may also be useful for reducing one or more symptoms of or for treating synucleopathies, infectious diseases, and sepsis and for enhancing a response to vaccination.

"Administer" as used herein includes administration of a disclosed peptide or modified version thereof itself as well as administration by various vehicles described below.

In some embodiments, one or more of the disclosed peptides and/or modified versions thereof, are directly administered. In some of these embodiments, a peptide carrier system is used. A number of peptide carrier systems are known in the art, including microparticles, polymeric nanoparticles, liposomes, solid lipid nanoparticles, hydrophilic mucoadhesive polymers, thiolated polymers, polymer matrices, nanoemulsions, and hydrogels. See Patel et al. (2014), Bruno et al. (2013), Feridooni et al. (2016). Any suitable system can be used.

In some embodiments, an engineered T cell that expresses and secretes one or more disclosed peptides can be used to deliver LAG3 inhibition at the site of engagement of the T cell receptor with an antigen. The T cell-based therapy can be, for example, a CAR-T cell that expresses one or more of the disclosed peptides. Either inducible or constitutive expression can be used.

In some embodiments, an oncolytic virus can be used to deliver one or more of the disclosed peptides. Either inducible or constitutive expression can be used.

In other embodiments one or more of the disclosed peptides are delivered using one or more nucleic acids encoding the peptide(s) (e.g., DNA, cDNA, PNA, RNA or a combination thereof); see, e.g., US 2017/0165335. Nucleic acids encoding one or more peptides can be delivered using a variety of delivery systems known in the art. Nucleic acid delivery systems include, but are not limited to, gene-gun; cationic lipids and cationic polymers; encapsulation in liposomes, microparticles, or microcapsules; electroporation; virus-based, and bacterial-based delivery systems. Virus-based systems include, but are not limited to, modified viruses such as adenovirus, adeno-associated virus, herpes virus, retroviruses, vaccinia virus, or hybrid viruses containing elements of one or more viruses. US 2002/0111323 describes use of "naked DNA," i.e., a "non-infectious, non-immunogenic, non-integrating DNA sequence," free from "transfection-facilitating proteins, viral particles, liposomal formulations, charged lipids and calcium phosphate precipitating agents," to administer a peptide. Bacterial-based delivery systems are disclosed, e.g., in Van Dessel et al. (2015) and Yang et al. (2007).

In some embodiments, a peptide is administered via an RNA molecule encoding the peptide. In some embodiments, the RNA molecule is encapsulated in a nanoparticle. In some embodiments, the nanoparticle comprises a cationic polymer (e.g., poly-L-lysine, polyamidoamine, polyethyleneimine, chitosan, poly(β-amino esters). In some embodiments, the nanoparticle comprises a cationic lipid or an ionizable lipid. In some embodiments, the RNA molecule is conjugated to a bioactive ligand (e.g., N-acetylgalactosamine (GalNAc), cholesterol, vitamin E, antibodies, cell-penetrating peptides). See, e.g., Akinc et al. (2008), Akinc et al. (2009), Anderson et al. (2003), Behr (1997), Boussif et al. (1995), Chen et al. (2012), Dahlman et al. (2014), Desigaux et al. (2007), Dong et al. (2014), Dosta et al. (2015), Fenton et al. (2016), Guo et al. (2012), Howard et al. (2006), Kaczmarek et al. (2016), Kanasty et al. (2013), Kauffman et al. (2015), Kozielski et al. (2013), Leus et al. (2014), Lorenz et al. (2004), Love et al. (2010), Lynn & Langer (2000), Moschos et al. (2007), Nair et al. (2014), Nishina et al. (2008), Pack et al. (2005), Rehman et al. (2013), Schroeder et al. (2010), Tsutsumi et al. (2007), Tzeng et al. (2012), Won et al. (2009), Xia et al. (2009), Yu et al. (2016).

In some embodiments, an RNA molecule can be modified to reduce its chances of degradation or recognition by the immune system. The ribose sugar, the phosphate linkage, and/or individual bases can be modified. See, e.g., Behlke (2008), Bramsen (2009), Chiu (2003), Judge & MacLachlan (2008), Kauffman (2016), Li (2016), Morrissey (2005), Prakash (2005), Pratt & MacRae (2009), Sahin (2014), Soutschek (2004), Wittrup & Lieberman (2015). In some embodiments, the modification is one or more of inclusion of a ribo-difluorotoluyl nucleotide, a 4'-thio modified RNA, a boranophosphate linkage, a phosphorothioate linkage, a 2'-O-methyl (2'-OMe) sugar substitution, a 2'-fluoro (2'-F), a 2'-O-methoxyethyl (2'-MOE) sugar substitution, a locked nucleic acid (LNA), and an L-RNA.

In some embodiments, administration is carried out in conjunction with one or more other therapies. "In conjunction with" includes administration together with, before, or after administration of the one or more other therapies.

Pharmaceutical Compositions, Routes of Administration, and Devices

One or more peptides, modified peptides, nucleic acid molecules, CAR-T cells, and/or oncolytic viruses, as discussed above, are typically administered in a pharmaceutical composition comprising a pharmaceutically acceptable vehicle. The "pharmaceutically acceptable vehicle" may comprise one or more substances which do not affect the biological activity of the peptides or modified versions thereof and, when administered to a patient, does not cause an adverse reaction. Pharmaceutical compositions may be liquid or may be lyophilized. Lyophilized compositions may be provided in a kit with a suitable liquid, typically water for injection (WFI) for use in reconstituting the composition. Other suitable forms of pharmaceutical compositions include suspensions, emulsions, and tablets.

Pharmaceutical compositions can be administered by any suitable route, including, but not limited to, intravenous, intramuscular, intradermal, intraperitoneal, subcutaneous, epidural, intratumoral, transdermal (e.g., US 2017/0281672), mucosal (e.g., intranasal or oral), pulmonary, and topical (e.g., US 2017/0274010) routes. See, e.g., US 2017/0101474.

Administration can be systemic or local. In addition to local infusions and injections, implants can be used to achieve a local administration. Examples of suitable materials include, but are not limited to, sialastic membranes, polymers, fibrous matrices, and collagen matrices.

Topical administration can be by way of a cream, ointment, lotion, transdermal patch (such as a microneedle patch), or other suitable forms well known in the art.

Administration can also be by controlled release, for example, using a microneedle patch, pump and/or suitable polymeric materials. Examples of suitable materials include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters.

Devices comprising any of the peptides, modified peptides, nucleic acid molecules, CAR-T cells, and/or oncolytic viruses described above include, but are not limited to, syringes, pumps, transdermal patches, spray devices, vaginal rings, and pessaries.

Treatment of Hyperproliferative Disorders, Including Cancer

In some embodiments, one or more of the peptides, modified peptides, nucleic acid molecules, CAR-T cells, and/or oncolytic viruses described above are administered to a patient to inhibit the progression of a hyperproliferative disorder, including cancer. Such inhibition may include, for example, reducing proliferation of neoplastic or pre-neoplastic cells; destroying neoplastic or pre-neoplastic cells; and inhibiting metastasis or decreasing the size of a tumor.

Examples of cancers include, but are not limited to, melanoma (including cutaneous or intraocular malignant melanoma), renal cancer, prostate cancer, breast cancer, colon cancer, lung cancer, bone cancer, pancreatic cancer, skin cancer, cancer of the head or neck, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, and T-cell lymphoma.

Combination Cancer Therapies

In some embodiments, one or more of the peptides, modified peptides, nucleic acid molecules, CAR-T cells, and/or oncolytic viruses described above are administered in conjunction with one or more other cancer therapies or immunotherapies, such as those described below.

In some embodiments, the second therapy comprises a second agent that reduces or blocks the activity of PD-1 (e.g., nivolumab, pembrolizumab, durvalumab) or CTLA-4 (e.g., ipilimumab, tremelimumab).

In some embodiments, the second therapy comprises an agent that reduces or blocks the activity of PD-L1 (e.g., atezolizumab).

In some embodiments, the second therapy comprises an agent that reduces or blocks the activity of LAG3 or other inhibitory checkpoint molecules and/or molecules that suppress the immune system. These molecules include, but are not limited to:

1. V-domain Immunoglobulin Suppressor of T cell Activation (VISTA, also known as c10orf54, PD-1H, DD1α, Gi24, Dies1, and SISP1; see US 2017/0334990, US 2017/0112929, Gao et al., 2017, Wang et al., 2011; Liu et al., 2015);
2. T-cell Immunoglobulin domain and Mucin domain 3 (TIM-3; see US 2017/0198041, US 2017/0029485, US 2014/0348842, Sakuishi et al., 2010);
3. killer immunoglobulin-like receptors (KIRs; see US 2015/0290316);
4. agents that inhibit indoleamine (2,3)-dioxygenase (IDO; see Mellemgaard et al., 2017);
5. B and T Lymphocyte Attenuator (BTLA; see US 2016/09222114); and
6. A2A adenosine receptor (A2AR; see Beavis et al., 2015; US 2013/0267515; US 2017/0166878; Leone et al., 2015; Mediavilla-Varela et al., 2017; Young et al., 2016).

Agents that reduce or block the activity of LAG3 include, but are not limited to, BMS-986016, IMP321, and GSK2831781 (He et al., 2016).

Agents that reduce or block the activity of VISTA include, but are not limited to, small molecules, such as CA-170, and antibodies (e.g., Le Mercier et al., 2014).

Agents that reduce or block the activity of TIM-3 include, but are not limited to, antibodies such as MBG453 and TSR-022; see Dempke et al., 2017.

Agents that reduce or block the activity of KIRs include, but are not limited to, monoclonal antibodies such as IPH2101 and Lirilumab (BMS-986015, formerly IPH2102); see Benson & Caligiuri, 2014.

Agents that reduce or block the activity of IDO include, but are not limited to, epacadostat and agents disclosed in US 2017/0037125.

Agents that reduce or block the activity of BTLA include, but are not limited to, peptides (e.g., Spodzieja et al., 2017).

Agents that reduce or block the activity of A2AR include, but are not limited to, small molecules such as CPI-444 and vipadenant.

In some embodiments, the second therapy comprises a cytokine (e.g., interleukin 7).

In some embodiments, the second therapy comprises an agonist of a stimulatory checkpoint molecule. These molecules include, but are not limited to:
1. CD40;
2. OX40;
3. glucocorticoid-induced tumor necrosis factor-related protein (GITR); and
4. Inducible T-cell COStimulator (ICOS).

Agonists of CD40 include, but are not limited to, CD40 agonist monoclonal antibodies such as cp-870,893, Chi-Lob7/4, dacetuzumab, and lucatumumab. See, e.g., Vonderheide et al., 2007; Khubchandani et al., 2009; Johnson et al., 2010; Bensinger et al., 2012; Vonderheide and Glennie, 2013; Johnson et al., 2015.

Agonists of OX40 include, but are not limited to, OX40 agonist antibodies such as MOXR0916, MED16469, MED10562, PF-045618600, GSK3174998, and INCCAGN01949, and OX40L-Fc fusion proteins, such as MEDI6383. See, e.g., Huseni et al., 2014; Linch et al., 2015; Messenheimer et al., 2017. See also Shrimali et al., 2017.

Agonists of GITR include, but are not limited to, MEDI1873. See, e.g., Schaer et al., 2012; Tigue et al., 2017.

Agonists of ICOS include, but are not limited to, ICOS agonist antibodies JTX-2011 and GSK3359609. See, e.g., Harvey et al., 2015; Michaelson et al., 2016.

In other embodiments, the second therapy comprises a 4-1BB agonist (Shindo et al., 2015), such as urelumab; a 4-1BB antagonist (see US 2017/0174773); an inhibitor of anaplastic lymphoma kinase (ALK; Wang et al., 2014; US 2017/0274074), such as crizotinib, ceritinib, alectinib, PF-06463922, NVP-TAE684, AP26113, TSR-011, X-396, CEP-37440, RXDX-101; an inhibitor of histone deacetylase (HDAC; see US 2017/0327582); a VEGFR inhibitor, such as axitinib, sunitinib, sorafenib, tivozanib, bevacizumab; and/or an anti-CD27 antibody, such as varlilumab.

In some embodiments, the second therapy comprises a cancer vaccine (e.g., Duraiswamy et al., 2013). A "cancer vaccine" is an immunogenic composition intended to elicit an immune response against a particular antigen in the individual to which the cancer vaccine is administered. A cancer vaccine typically contains a tumor antigen which is able to induce or stimulate an immune response against the tumor antigen. A "tumor antigen" is an antigen that is present on the surface of a target tumor. A tumor antigen may be a molecule which is not expressed by a non-tumor cell or may be, for example, an altered version of a molecule expressed by a non-tumor cell (e.g., a protein that is misfolded, truncated, or otherwise mutated).

In some embodiments, the second therapy comprises a chimeric antigen receptor (CAR) T cell therapy. See, e.g., John et al., 2013; Chong et al., 2016.

In some embodiments, one or more of the peptides, modified peptides, nucleic acid molecules, CAR-T cells, and/or oncolytic viruses described above are administered in conjunction with a CAR-T cell cancer therapy to increase the efficacy of the CAR-T cell cancer therapy.

In some embodiments, one or more of the peptides, modified peptides, nucleic acid molecules, CAR-T cells, and/or oncolytic viruses described above are administered in conjunction with an oncolytic virus as disclosed, for example, in US 2017/0143780. Non-limiting examples of oncolytic viruses are described above.

Additional Therapeutic Uses

Synucleinopathies

In some embodiments, one or more of the peptides, modified peptides, nucleic acid molecules, CAR-T cells, and/or oncolytic viruses described above may be useful to reduce a symptom of a synucleinopathy, either alone or in combination with other therapeutic interventions such as L-DOPA, dopamine agonists (e.g., ropinirole, pramipexole), dopamine reuptake inhibitors (e.g., amantadine), and cholinesterase inhibitors (e.g., donepezil, rivastigmine, galantamine). Examples of synucleinopathies include idiopathic and inherited forms of Parkinson's disease (PD); diffuse Lewy body (DLB) disease, also known as dementia with Lewy bodies or Lewy body dementia; incidental Lewy body disease; Lewy body variant of Alzheimer's disease (LBV); combined Alzheimer's and Parkinson disease (CAPD); pure autonomic failure (PAF); multiple system atrophy (MSA), such as olivopontocerebellar atrophy, striatonigral degeneration, and Shy-Drager Syndrome; pantothenate kinase-associated neurodegeneration; Down's Syndrome; Gaucher disease-related synucleinopathies; and neurodegeneration with brain iron accumulation.

Sepsis

LAG3 expression is up-regulated in sepsis (Patil et al., 2017). Accordingly, one or more of the peptides, modified peptides, or nucleic acids described above may be useful to treat sepsis, either alone or in combination with other therapeutic interventions such as antibiotics, intravenous fluids, and vasopressors.

Infectious Diseases

In some embodiments, one or more of the disclosed peptides, modified peptides, or nucleic acids described above can be administered to treat infectious diseases, including chronic infections, caused, e.g., by viruses, fungi, bacteria, and protozoa, and helminths, either alone or in combination with other therapeutic interventions.

Examples of viral agents include human immunodeficiency virus (HIV), Epstein Barr Virus (EBV), Herpes simplex (HSV, including HSV1 and HSV2), Human Papillomavirus (HPV), Varicella zoster (VSV) Cytomegalovirus (CMV), and hepatitis A, B, and C viruses.

Examples of fungal agents include *Aspergillus, Candida, Coccidioides, Cryptococcus*, and *Histoplasma capsulatum.*

Examples of bacterial agents include Streptococcal bacteria (e.g., *pyogenes, agalactiae, pneumoniae*), *Chlamydia pneumoniae, Listeria monocytogenes*, and *Mycobacterium tuberculosis.*

Examples of protozoa include Sarcodina (e.g., *Entamoeba*), *Mastigophora* (e.g., *Giardia*), *Ciliophora* (e.g., *Balantidium*), and Sporozoa (e.g., *Plasmodium falciparum, Cryptosporidium*).

Examples of helminths include Platyhelminths (e.g., trematodes, cestodes), Acanthocephalins, and Nematodes.

Vaccine Adjuvants

In some embodiments one or more of the disclosed peptides, modified peptides, or nucleic acids described above can be administered as a vaccine adjuvant in conjunction with a vaccine to enhance a response to vaccination (e.g., by increasing effector T cells and/or reducing T cell exhaustion). The vaccine can be, for example, an RNA vaccine (e.g., US 2016/0130345, US 2017/0182150), a DNA vaccine, a recombinant vector, a protein vaccine, or a peptide vaccine. Such vaccines can be delivered, for example, using virus-like particles, as is well known in the art.

EXAMPLE 1. Peptide Library Screening

The TriCo-20™, TriCo-16™, Ph.D.-12™, and Ph.D. C7™ Phage Display Peptide Libraries (Creative Biolabs, 45-1 Ramsey Road, Shirley, NY 11967) were screened by performing several rounds of bio-panning to identify binders of soluble recombinant human LAG3.

After four rounds of screening, seven peptides showed clear enrichment for specific binders as defined by greater than 2-fold higher coated signal over uncoated signal in the clonal phage ELISA (Table 2).

TABLE 2

| Clonal Phase ELISA | | | |
| --- | --- | --- | --- |
| clone | coated signal | uncoated signal | peptide sequence | SEQ ID NO: |
| LAG3-11 | 0.271 | 0.093 | SAPWEPLHWPEDWWQGTGEW | 1 |
| LAG3-42 | 0.378 | 0.084 | DWNFQQWDWKKHNHLDSHVV | 2 |
| LAG3-48 | 0.227 | 0.094 | FYSPNHEEYHDWNVDSSVNE | 3 |
| LAG3-51 | 0.234 | 0.076 | KVWQVPQDTQHWLSPNFYSV | 4 |
| LAG3-54 | 0.417 | 0.103 | ACGPGSFGDCGGG | 5 |
| LAG3-56 | 0.529 | 0.101 | HIQNWSYWLNQDMMNQQVWKS | 6 |
| LAG3-60 | 0.330 | 0.091 | HESGSVPHPWQFFTHYVS | 7 |

EXAMPLE 2. Peptide Blockage of LAG3 Signaling

A cell-based reporter assay was used to assess whether binding of the seven peptides identified above was sufficient to block the interaction with LAG3 and its ligand MHC-II. The components of the assay include (1) a Jurkat T cell line that stably expresses human LAG3 and a stable NFAT-luc2P luciferase reporter, (2) a Raji cell line that expresses human MHC-II, and (3) a positive control anti-LAG3 antibody that blocks the interaction of LAG3 and MHC-II. In brief, Jurkat cells expressing LAG3 are stimulated with a T cell receptor (TCR) activator molecule, resulting in expression of luciferase. When the Jurkat cells are co-cultured with an a Raji cell line expressing the MHC-II molecule, the interaction of LAG3 on the surface of a Jurkat cell with MHC-II on the surface of a Raji cell inhibits T cell activation, leading to a reduction in luciferase expression. The addition of a neutralizing antibody against LAG3 blocks the inhibition signal and allows luciferase expression to proceed. BIO-GLO™ (Promega) was used to measure luciferase expression. The seven LAG3 peptides were tested at concentrations of 0, 0.64, 1.6, 4, 10, 25, & 100 M.

Results of the positive control assay using the anti-LAG3 control antibody are shown in FIG. 1A. These results demonstrate that the control antibody restores luciferase expression in a dose-dependent manner, with peak-fold inhibition of approximately 5 at an antibody concentration of 25 µg/ml.

Figure 1B:
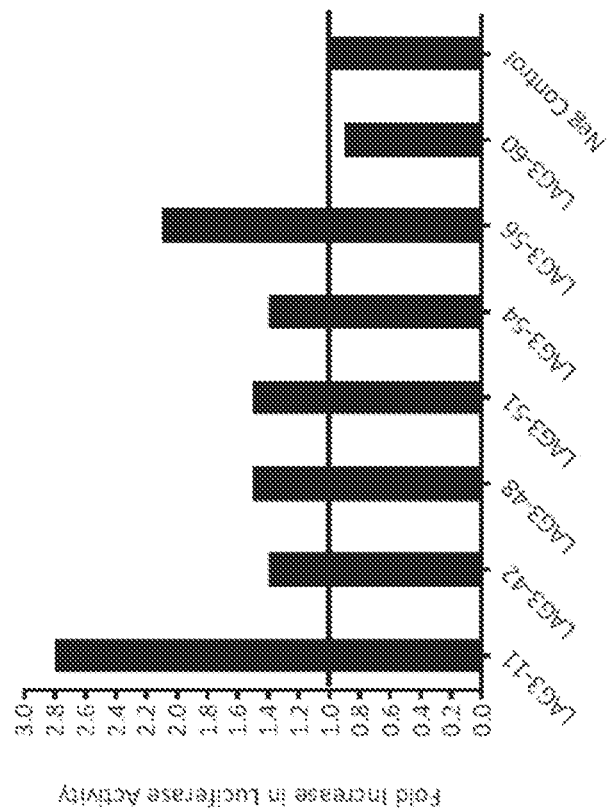
Figure 2A:
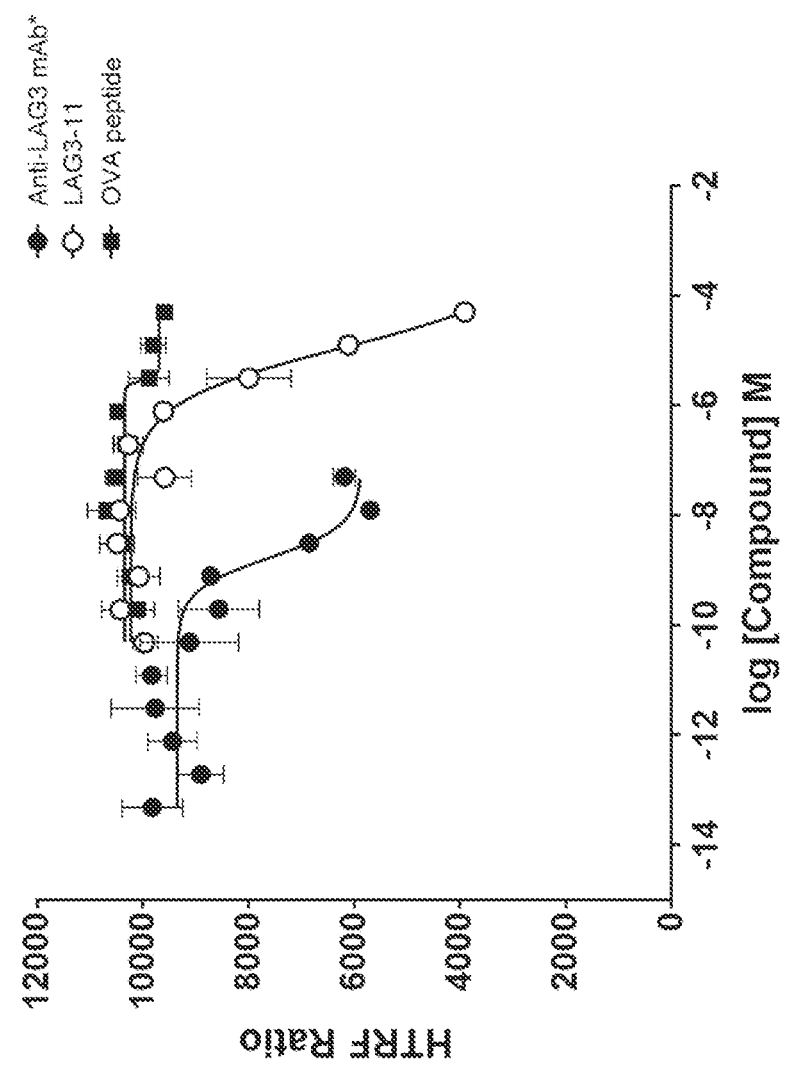
FIG. 2 is a graph showing the results of a homogeneous time-resolved fluorescence (HTRF) assay for peptide LAG3-11. Reference Ab-LAG3 is an anti-LAG3 antibody. OVA, the ovalbumin (OVA) peptide (ISQAVHAAHAEINEAGR, SEQ ID NO:8). "HTRF ratio" is the emission at 665 nm (acceptor)/emission at 620 nm (donor) multiplied by a factor or $10^4$.
Figure 2B:
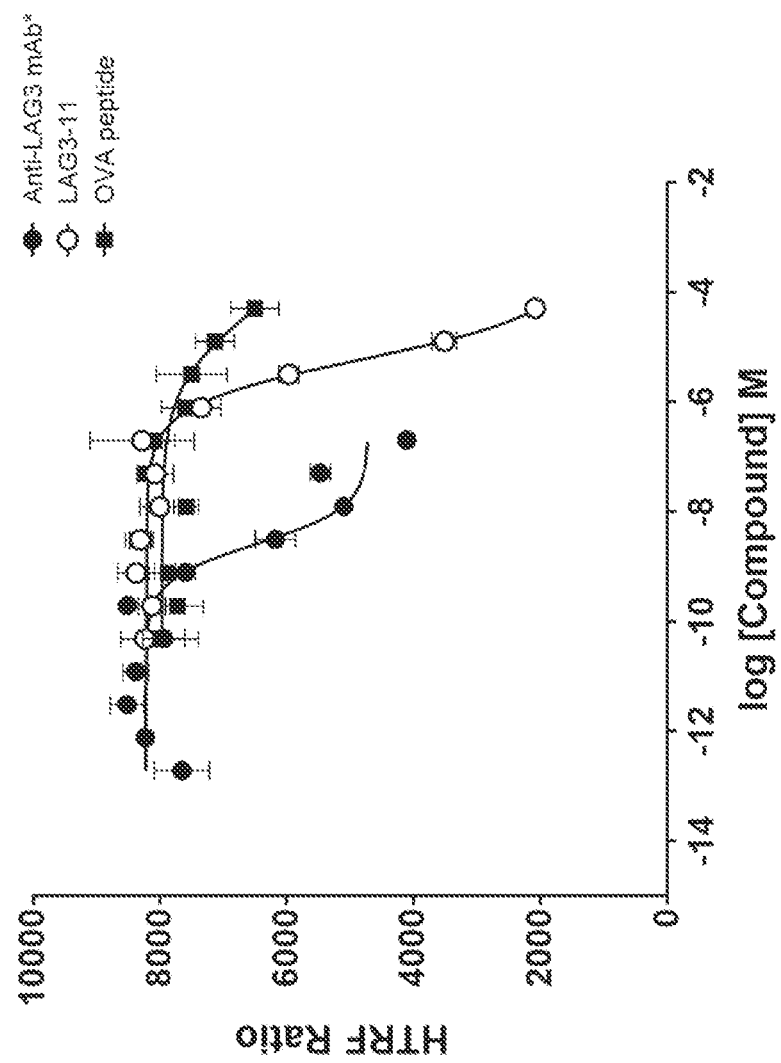
Figure 2C:
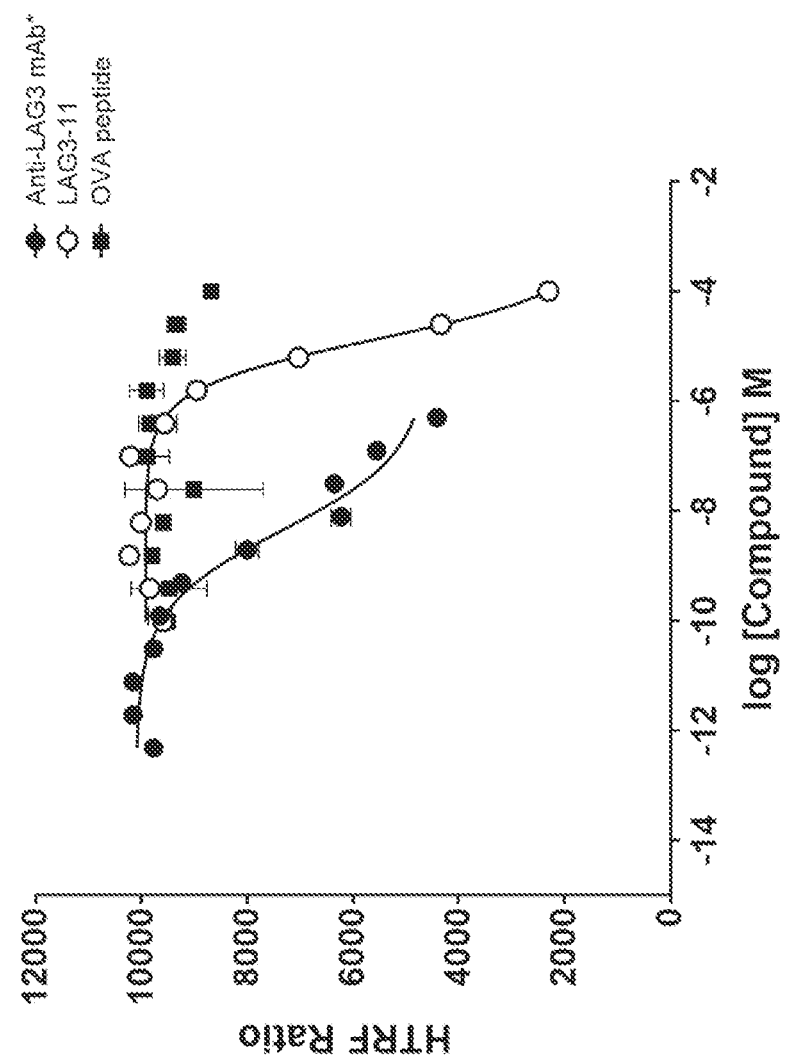
Figure 2D:
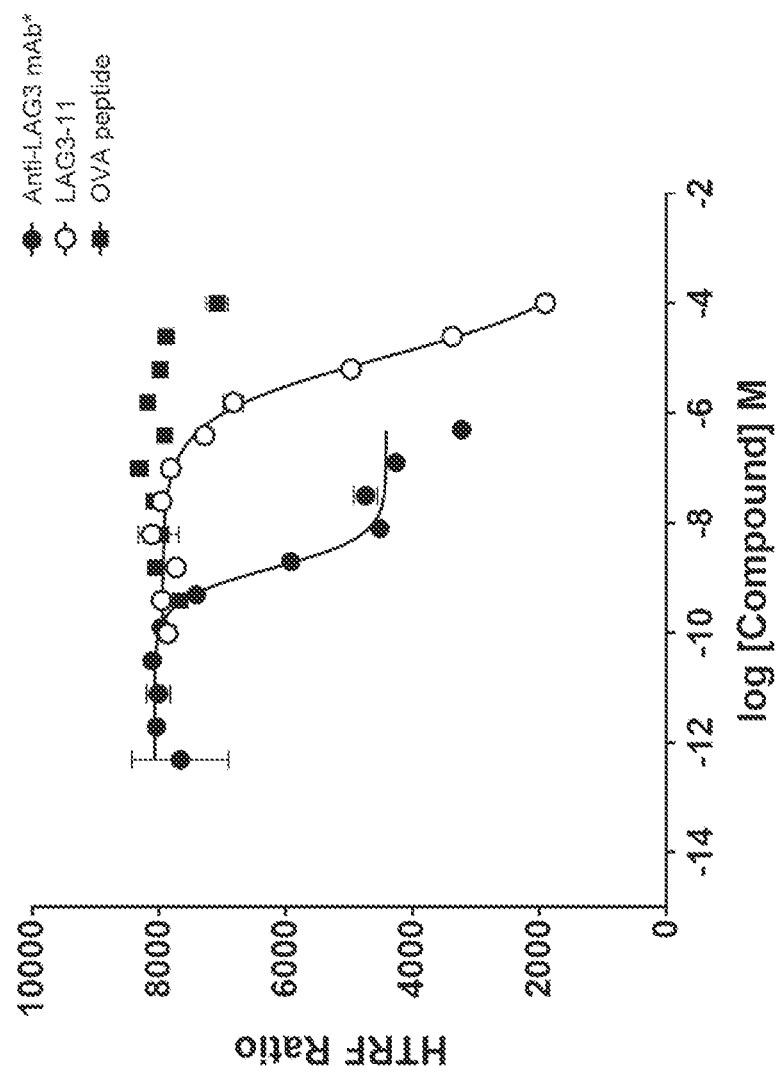
Figure 3:
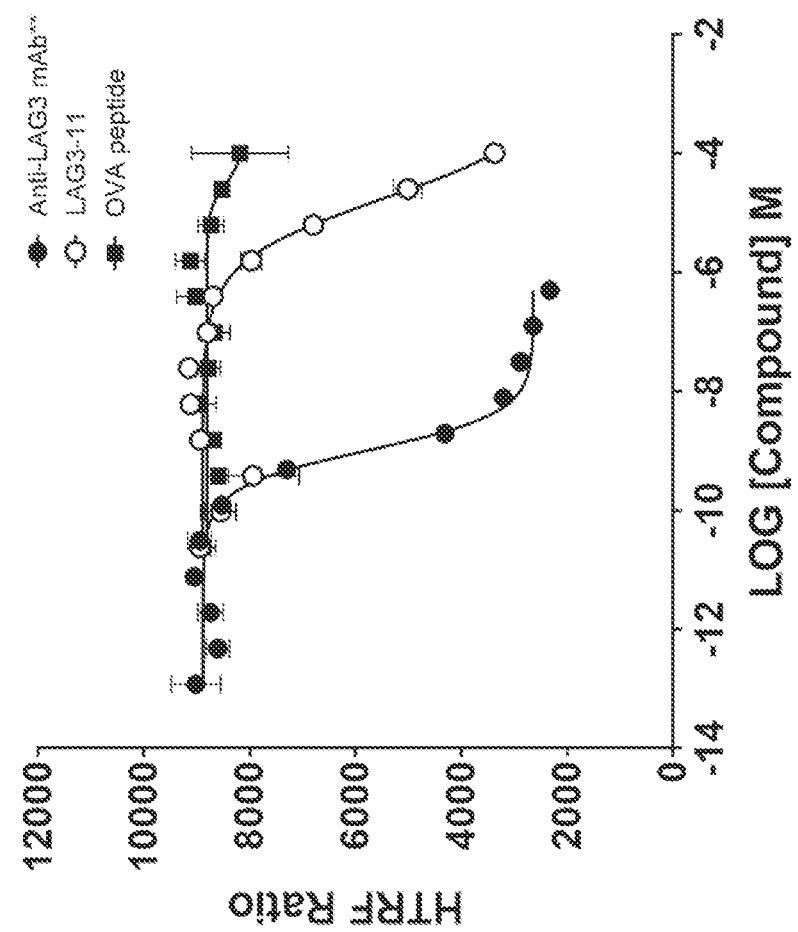
FIG. 3 is a graph showing the results of an HTRF assay for peptide LAG3-11. Anti-LAG-3 GMP-A092 is an anti-LAG3 antibody.
Figure 4:
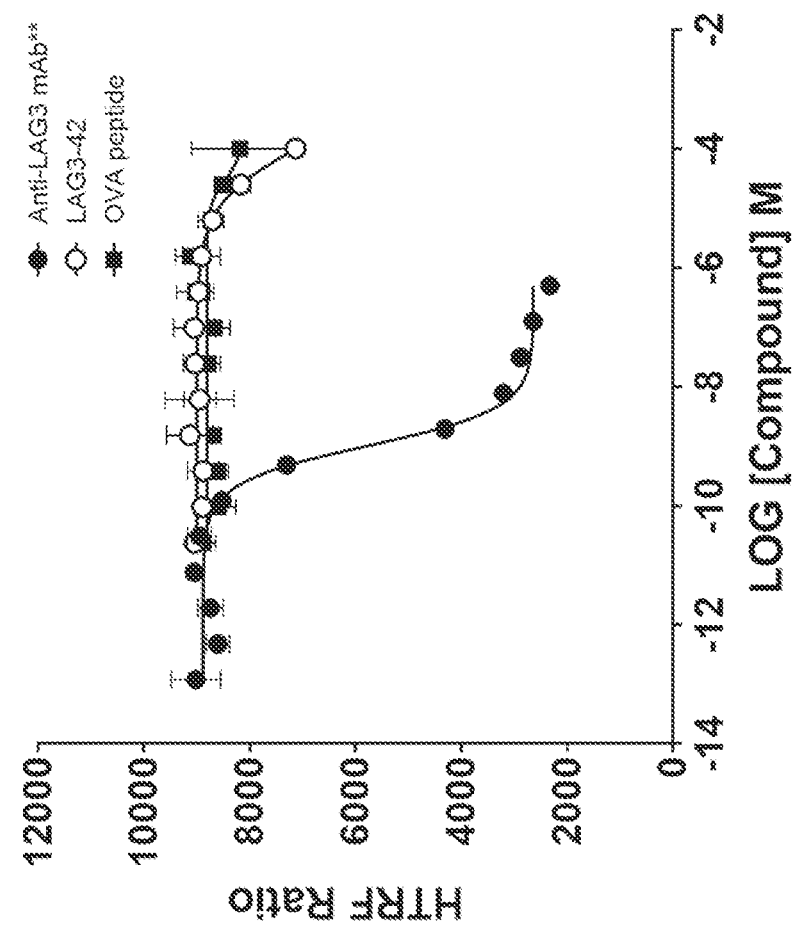
FIG. 4 is a graph showing the results of an HTRF assay for peptide LAG3-42.
Figure 5:
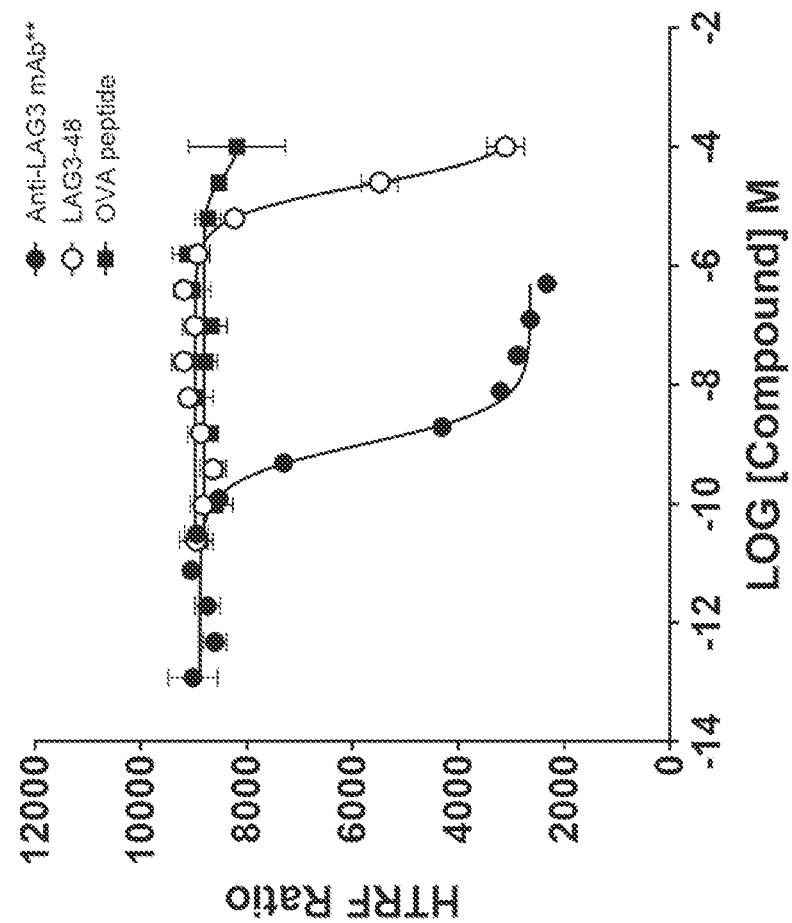
FIG. 5 is a graph showing the results of an HTRF assay for peptide LAG3-48.
Figure 6:
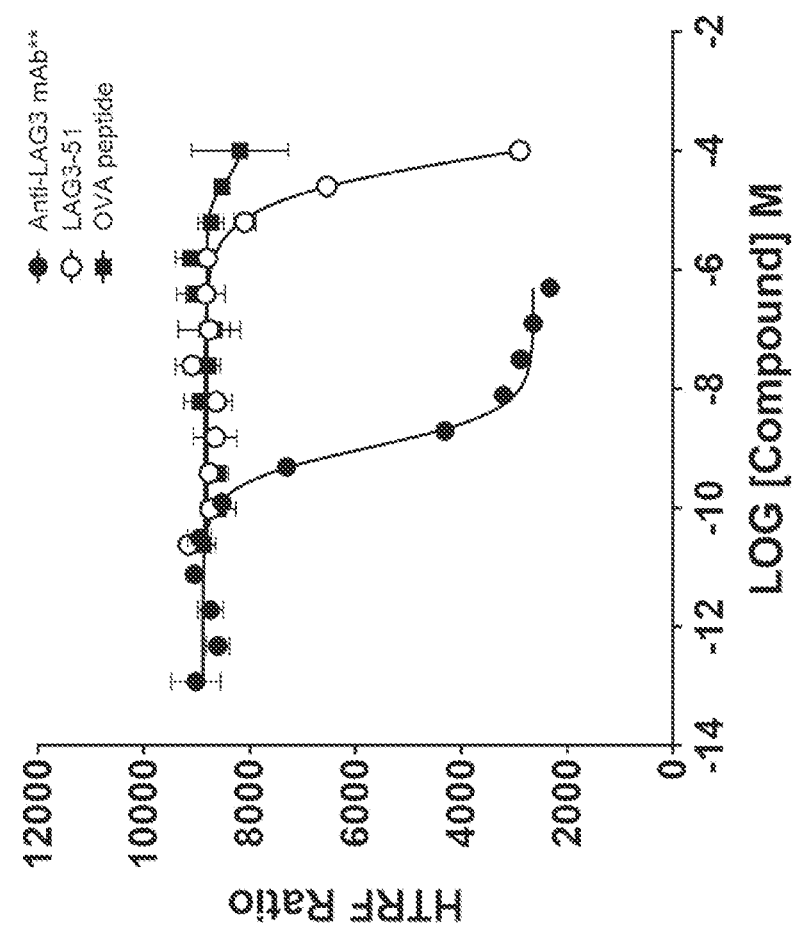
FIG. 6 is a graph showing the results of an HTRF assay for peptide LAG3-51.
Figure 7:
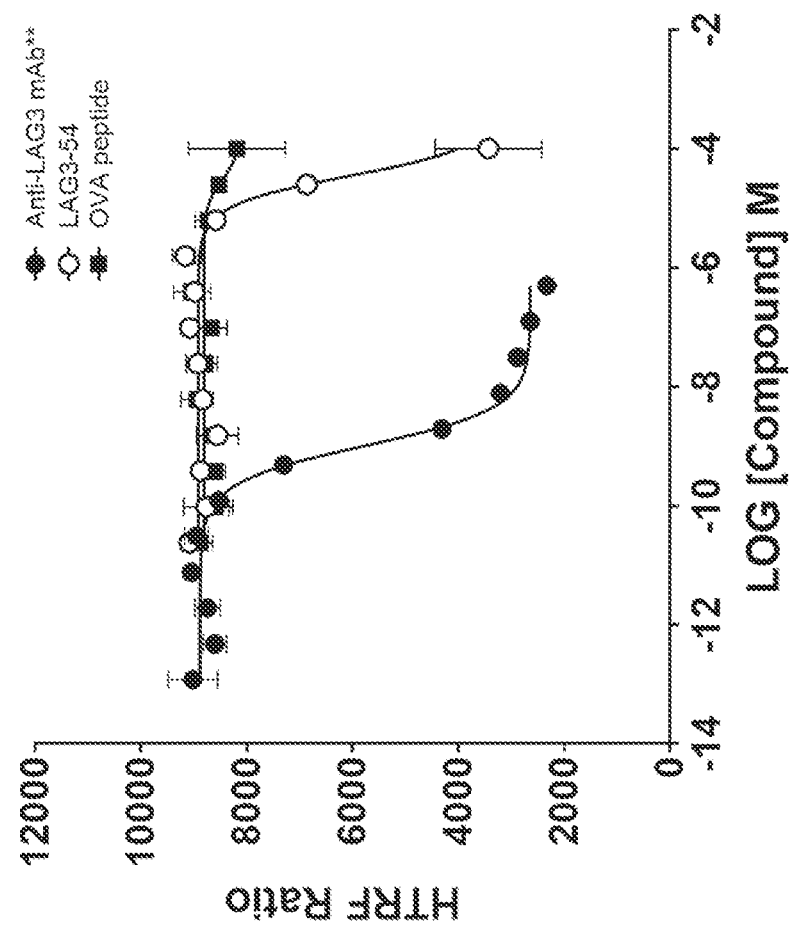
FIG. 7 is a graph showing the results of an HTRF assay for peptide LAG3-54.
Figure 8:
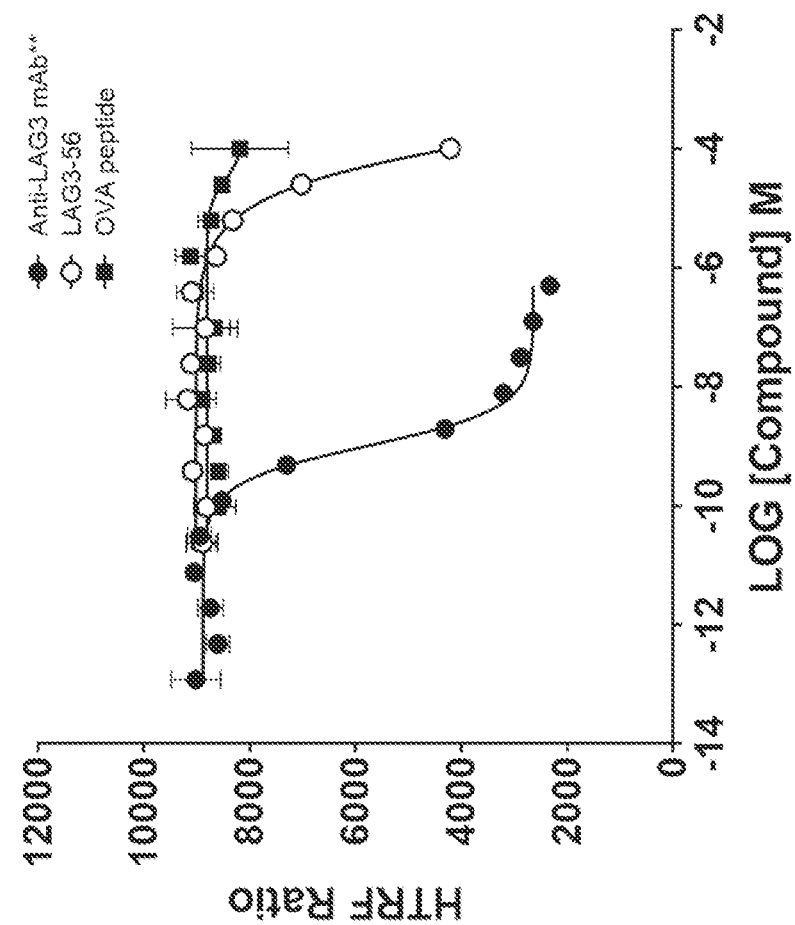
FIG. 8 is a graph showing the results of an HTRF assay for peptide LAG3-56.

Results of the assay testing the seven LAG3 peptides identified above and a negative control peptide (SSYHHFKMPELHFGKNTFHQ; SEQ ID NO:9) are shown in FIG. 1B. These data are presented as fold increase in luciferase activity, where for each peptide the relative light units (RLUs) measured at 100 M was compared to the RLUs measured at 0.64 M. The results demonstrate that two of the peptides, LAG3-11 and LAG3-56, restore luciferase expression with fold inhibition of approximately 2.8 and 2.2, respectively, at a concentration of 100 M.

EXAMPLE 3. Peptide Disruption of LAG3-MHC-II Interaction

A homogeneous time-resolved fluorescence (HTRF) LAG3/MHC-II binding assay (Cisbio US Inc.) was used to measure the interaction between MHC-II and LAG3 in the presence of peptides. In this assay, the interaction between Tag1-LAG3 and Tag2-MHC-II is detected by using anti-Tag1-Terbium (HTRF donor) and anti-Tag2-XL665 (HTRF acceptor). When the donor and acceptor antibodies are brought into close proximity due to LAG3 and MHC-II binding, excitation of the donor antibody triggers fluorescent resonance energy transfer (FRET) towards the acceptor antibody, which in turn emits specifically at 665 nm. This specific signal is directly proportional to the extent of LAG3/MHC-II interaction. Thus, an agent that blocks the interaction between LAG3 and MHC-II will cause a reduction in HTRF ratio.

An anti-human LAG3 antibody (Novoprotein #GMP-A092, Lot 0331158, 500 nM) was tested in the assay at an eleven-point, serially diluted semi-log dose response curve starting at 100 nM and served as a positive control. The ovalbumin peptide was used as a negative control. Peptides were reconstituted at a concentration of 20 mM in 100 µM DMSO and tested at an eleven-point dose response curve starting at 100 M followed by 4-fold dilutions. Each dose was tested in triplicate.

FIGS. 2A-D are graphs showing the results of four independent experiments testing peptide LAG3-11. These results demonstrate that peptide LAG3-11 disrupts the interaction of LAG3 and MHC-II.

Figure 9:
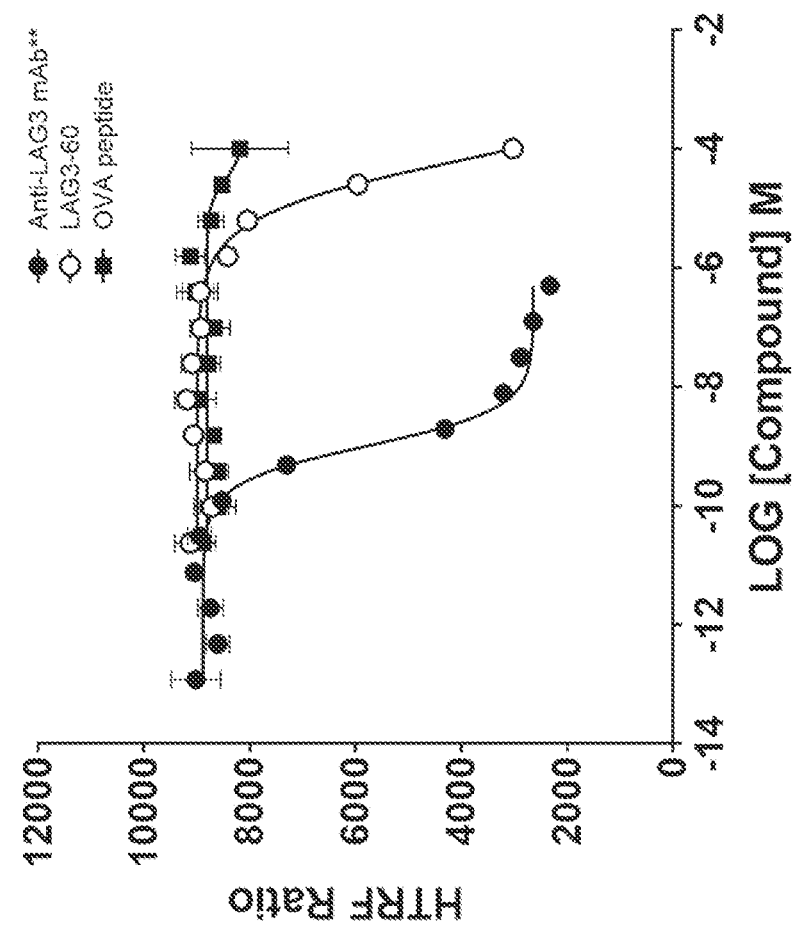
FIG. 9 is a graph showing the results of an HTRF assay for peptide LAG3-60.
Figure 10:
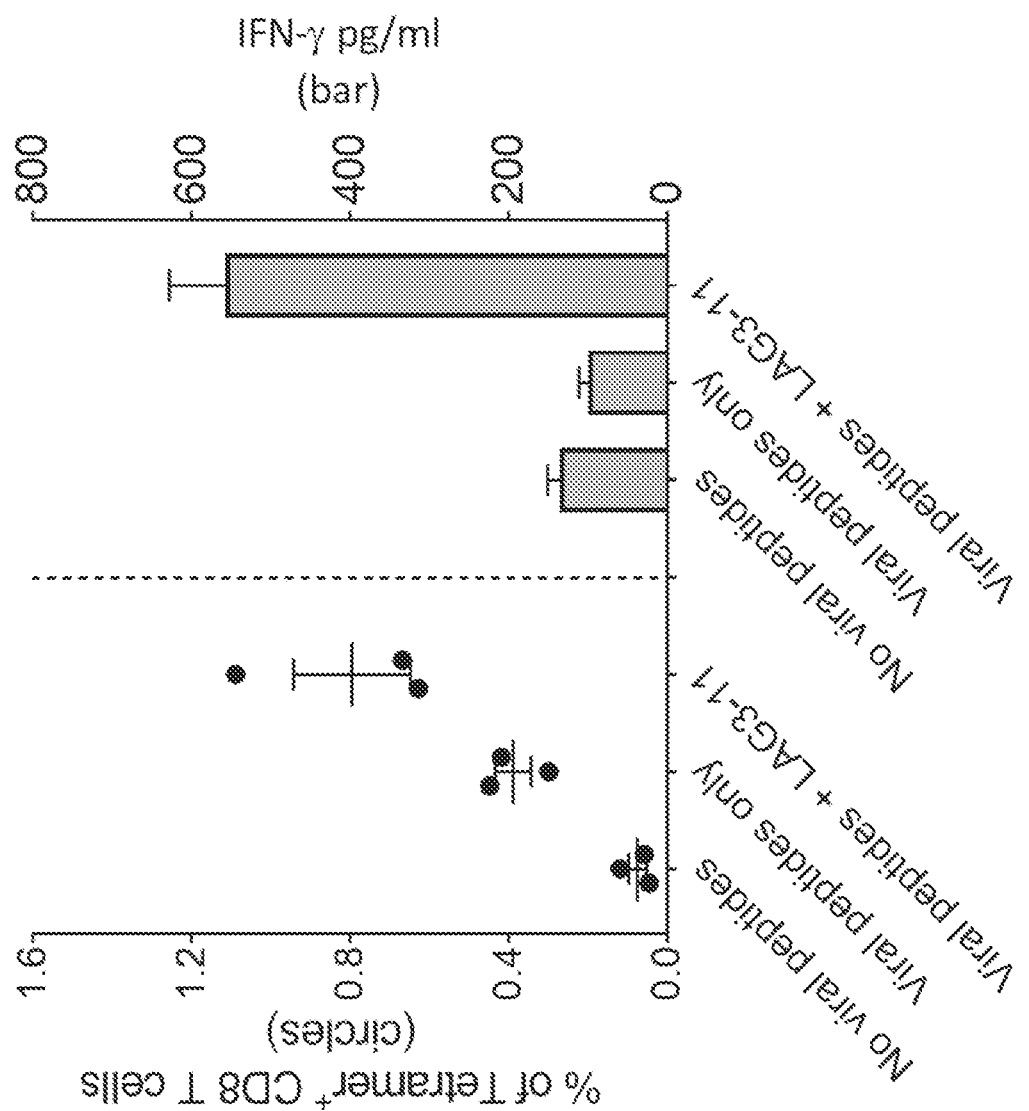
FIG. 10 is a graph showing the results of a peripheral blood mononuclear cell (PBMC) assay.

FIGS. 3-9 are graphs showing the results of experiments testing peptides LAG3-11 (FIG. 3), LAG3-42 (FIG. 4), LAG3-48 (FIG. 5), LAG3-51 (FIG. 6), LAG3-54 (FIG. 7), LAG3-56 (FIG. 8), and LAG3-60 (FIG. 9). The individual HTRF ratios used to construct these graphs are shown in Table 3A and Table 3B.

EXAMPLE 6. Interaction of Peptides with FGL1

This example demonstrates the ability of LAG-11 and LAG-56 to inhibit the interaction between human LAG3 and FGL1. The peptides were tested using a human LAG3/FGL1 TR-FRET binding assay (BPS Bioscience) carried out according to the manufacturer's instructions.

TABLE 3A

| LOG [Compound] M tested for Ab | LOG [Compound] M tested for peptide | Anti-LAG3 Ab plate 1 | | | Anti-LAG3 Ab plate 2 | | | OVA peptide | | | LAG3-11 | | | LAG3-42 | | |
|---|---|---|---|---|---|---|---|---|---|---|---|---|---|---|---|---|
| −6.30103 | −4 | 2261 | 2359 | 2383 | 2234 | 2090 | 2346 | 8492 | 8909 | 7154 | 3213 | 3460 | 3458 | 7234 | 7037 | 7142 |
| −6.90309 | −4.60206 | 2647 | 2555 | 2743 | 2551 | 2501 | 2502 | 8472 | 8683 | 8449 | 4749 | 5287 | 5014 | 8389 | 8097 | 8045 |
| −7.50515 | −5.20412 | 2867 | 2915 | 2884 | 2971 | 2846 | 2840 | 8616 | 8579 | 9015 | 6812 | 6892 | 6696 | 8629 | 8765 | 8733 |
| −8.10721 | −5.80618 | 3203 | 3242 | 3170 | 3397 | 3262 | 3125 | 8833 | 9374 | 9180 | 7774 | 8164 | 7993 | 9281 | 8905 | 8572 |
| −8.70927 | −6.40824 | 4160 | 4457 | 4334 | 4286 | 4196 | 4352 | 8634 | 9280 | 9189 | 8538 | 8718 | 8858 | 9189 | 8945 | 8784 |
| −9.31133 | −7.0103 | 7218 | 7408 | 7295 | 7240 | 7263 | 7467 | 8654 | 8970 | 8380 | 8794 | 8729 | 8889 | 9432 | 8649 | 9072 |
| −9.91339 | −7.61236 | 8483 | 8643 | 8452 | 8987 | 8533 | 8601 | 8776 | 8568 | 9015 | 9090 | 9036 | 9329 | 9209 | 8787 | 9109 |
| −10.5154 | −8.21442 | 9213 | 8795 | 8849 | 9499 | 9021 | 8595 | 8624 | 8987 | 9219 | 9012 | 9293 | 9067 | 9407 | 8205 | 9247 |
| −11.1175 | −8.81648 | 9027 | 9147 | 8987 | 9102 | 9305 | 8453 | 8724 | 8639 | 8684 | 8877 | 8955 | 8992 | 9579 | 9134 | 8703 |
| −11.7196 | −9.41854 | 9013 | 8676 | 8552 | 9004 | 9330 | 8893 | 8396 | 8788 | 8625 | 8591 | 6950 | 8287 | 9137 | 8550 | 8958 |
| −12.3216 | −10.0206 | 8724 | 8742 | 8355 | 8952 | 8717 | 8824 | 8986 | 8457 | 8356 | 8212 | 8748 | 8700 | 8860 | 8937 | 8907 |
| −12.9237 | −10.6227 | 8512 | 9425 | 9136 | 9058 | 8523 | 8363 | 9086 | 8892 | 8633 | 8886 | 8842 | 9097 | 9016 | 8914 | 9210 |

TABLE 3B

| LOG [Compound] M tested for Ab | LOG [Compound] M tested for peptide | LAG3-48 | | | LAG3-51 | | | LAG3-54 | | | LAG3-56 | | | LAG3-60 | | |
|---|---|---|---|---|---|---|---|---|---|---|---|---|---|---|---|---|
| −6.30103 | −4 | 3507 | 2809 | 3028 | 3058 | 2773 | 2875 | 4122 | 3912 | 2283 | 4194 | 4083 | 4373 | 2986 |  | 3079 |
| −6.90309 | −4.60206 | 5662 | 5088 | 5724 | 6649 | 6521 | 6468 | 6709 | 6833 | 7055 | 6880 | 7058 | 7142 | 5934 | 5959 | 5991 |
| −7.50515 | −5.20412 | 8301 | 8213 | 8200 | 7908 | 8071 | 8322 | 8561 | 8512 | 8691 | 8218 | 8349 | 8414 | 8233 | 7988 | 7918 |
| −8.10721 | −5.80618 | 8663 | 9082 | 9045 | 8723 | 8946 | 8748 | 9205 | 9142 | 9156 | 8791 | 8658 | 8464 | 8525 | 8398 | 8342 |
| −8.70927 | −6.40824 | 9264 | 9194 | 9135 | 9265 | 8583 | 8662 | 9048 | 8773 | 9161 | 9040 | 9185 | 9082 | 8614 | 8929 | 9290 |
| −9.31133 | −7.0103 | 8727 | 9103 | 9142 | 8098 | 9193 | 9017 | 9141 | 9004 | 9105 | 8147 | 9275 | 9111 | 9142 | 8745 | 8892 |
| −9.91339 | −7.61236 | 8936 | 9357 | 9297 | 8762 | 9360 | 9173 | 9031 | 9075 | 8674 | 8935 | 9303 | 9093 | 8987 | 8983 | 9320 |
| −10.5154 | −8.21442 | 9082 | 9139 | 9095 | 8950 | 8608 | 8357 | 8645 | 8867 | 8996 | 8765 | 9591 | 9178 | 9275 | 8931 | 9366 |
| −11.1175 | −8.81648 | 8708 | 9153 | 8757 | 8834 | 8187 | 8957 | 8918 | 8630 | 8130 | 8856 | 8856 | 8869 | 9059 | 9248 | 8887 |
| −11.7196 | −9.41854 | 8564 | 8922 | 8442 | 8867 | 8809 | 8630 | 8930 | 8755 | 8942 | 9050 | 9029 | 9176 | 8772 | 8594 | 9169 |
| −12.3216 | −10.0206 | 8765 | 9097 | 8602 | 8784 | 8779 | 8696 | 9203 | 8748 | 8344 | 9022 | 8887 | 8540 | 8924 | 8349 | 8904 |
| −12.9237 | −10.6227 | 8663 | 8904 | 9303 | 9082 | 9104 | 9298 | 9262 | 8921 | 9100 | 8885 | 9204 | 8617 | 8795 | 9240 | 9350 |

EXAMPLE 5. Peptide Enhancement of CD8+ T Cell Responses

This Example demonstrates the effect of peptide LAG3-11 on the IFN-7 secretion and proliferation in a human peripheral blood mononuclear cell (PBMC)-based recall assay. PBMCs were obtained from a human donor who had previously been identified as a positive responder to Epstein-Barr virus (EBV) and Cytomegalovirus (CMV) viral-specific peptides. $5 \times 10^5$ PBMCs in 200 μL of media were stimulated with EBV and CMV viral-specific peptides in the presence or absence of LAG3-11. Seven days post-stimulation, the percentage of virus-specific CD8+ T cells were identified via flow cytometry using MHC-I tetramers. Supernatants were also collected and the amount of IFN-7 determined via ELISA.

Figure 11:
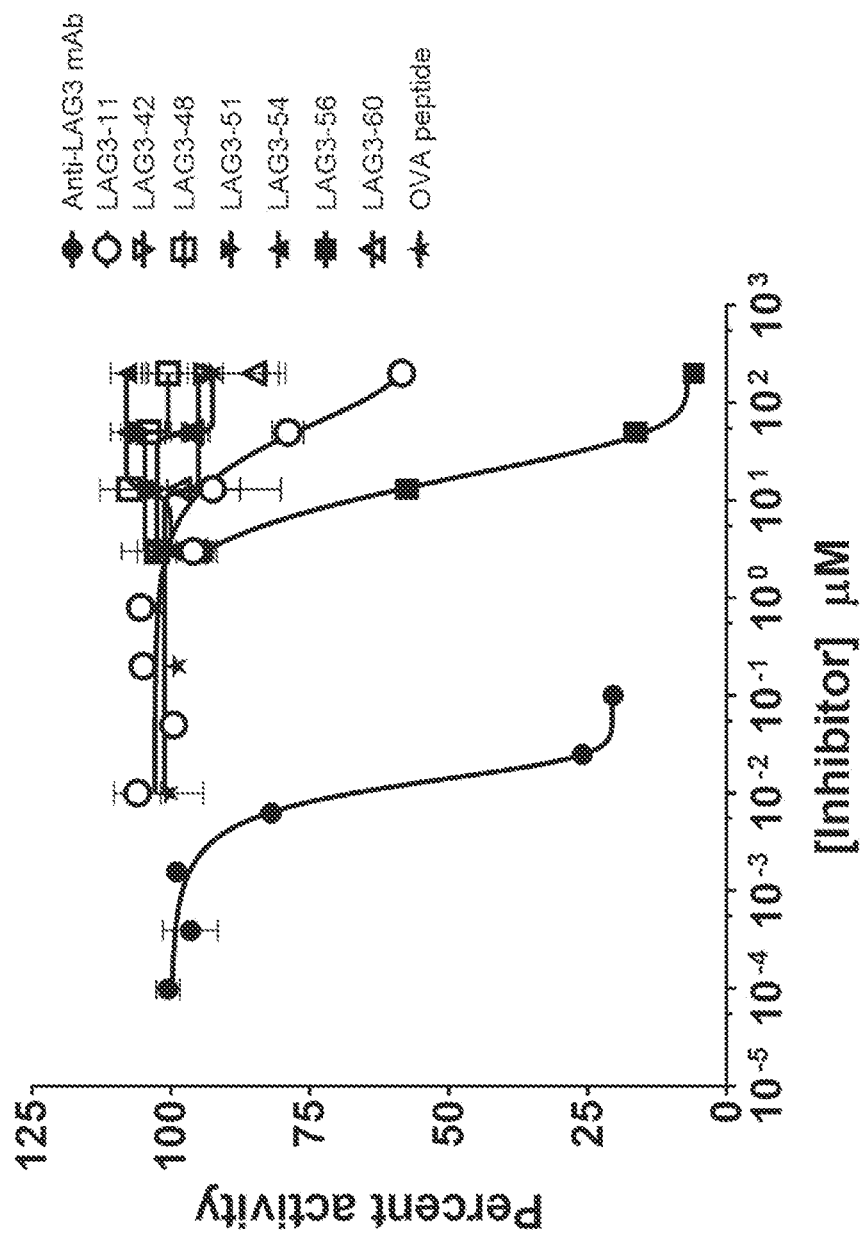
FIG. 11 is a graph showing the results of a human LAG3/FGL1 TR-FRET binding assay.

The results, shown in FIG. 11, demonstrate that LAG3-11 increases IFN-7 secretion by human PBMCs 3-fold relative to the viral-specific peptides alone. The ~2-fold increase in percentage of tetramer$^+$ CD8 T cells indicates that the LAG3-11 peptide may enhance T cell proliferation.

Peptide stocks of LAG3-11, LAG3-42, LAG3-48, LAG3-51, LAG3-54, LAG3-56, LAG3-60 and OVA were prepared at 1 mM followed by a 1:5 dilution in plate reactions. LAG3-11 and OVA were tested at 200, 50, 13, 3, 0.8, 0.2, 0.05, and 0.01 μM. The other peptides were tested at 200, 50, 13, and 3 μM. A neutralizing anti-human LAG3 antibody (BPS Bioscience Cat. #71219) was used as a positive control.

Reaction mixes were incubated 1 hr at RT before development. After development, plate was read in a Tecan M1000 TR-FRET instrument. Percent activity was calculated as follows:

% Activity=100×[(sample−minimum)/(maximum−minimum)]

The results are shown in FIG. 11.

REFERENCES

Adams et al., "Big opportunities for small molecules in immuno-oncology," Nature Reviews Drug Discovery Advance Online Publication, Jul. 31, 2016, 20 pages Akinc et al., "A combinatorial library of lipid-like materials for delivery of RNAi therapeutics," Nat. Biotechnol. 26, 561-69, 2008

Akinc et al., "Development of lipidoid-siRNA formulations for systemic delivery to the liver," Mol. Ther. 17, 872-79, 2009

Alsaab et al., "PD-1 and PD-L1 Checkpoint Signaling Inhibition for Cancer Immunotherapy: Mechanism, Combinations, and Clinical Outcome," Front. Pharmacol. 8, 561, 2017

Anderson et al., "semi-automated synthesis and screening of a large library of degradable cationic polymers for gene delivery," Angew. Chemi Int. Ed. 42, 3153-58, 2003

Andtbacka et al., "OPTiM: A randomized phase III trial of talimogene laherparepvec (T-VEC) versus subcutaneous (SC) granulocyte-macrophage colony-stimulating factor (GM-CSF) for the treatment (tx) of unresected stage IIIB/C and IV melanoma," J. Clin. Oncol. 31, abstract number LBA9008, 2013

Beavis et al., "Adenosine Receptor 2A Blockade Increases the Efficacy of Anti-PD-1 through Enhanced Antitumor T-cell Responses," Cancer Immunol. Res. 3, 506-17, 2015

Behlke, "Chemical modification of siRNAs for in vivo use," Oligonucleotides. 2008; 18:305-19.

Behr, "The proton sponge: a trick to enter cells the viruses did not exploit," Int. J. Chem. 2, 34-36, 1997

Bensinger et al., "A phase 1 study of lucatumumab, a fully human anti-CD40 antagonist monoclonal antibody administered intravenously to patients with relapsed or refractory multiple myeloma," Br J Haematol. 159, 58-66, 2012.

Benson & Caligiuri, "Killer Immunoglobulin-like Receptors and Tumor Immunity," Cancer Immunol Res 2014; 2:99-104

Bodanszky et al., Peptide Synthesis, John Wiley and Sons, 2d ed. (1976)

Boussif et al., "A versatile vector for gene and oligonucleotide transfer into cells in culture and in vivo: polyethylenimine," Proc. Nat'l. Acad. Sci. (USA) 92, 7297-301, 1995

Bramsen et al., "A large-scale chemical modification screen identifies design rules to generate siRNAs with high activity, high stability and low toxicity," Nucleic Acids Res. 2009; 37:2867-81

Bruno et al., "Basics and recent advances in peptide and protein drug delivery," Ther. Deliv. 4, 1443-67, 2013

Bu et al., "Learning from PD-1 Resistance: New Combination Strategies," Trends Mol. Med. 22, 448-51, 2016

Burnett & Rossi, "RNA-based Therapeutics-Current Progress and Future Prospects," Chem Biol. 19, 60-71, 2012

Cao, "Advances in Delivering Protein and Peptide Therapeutics," Pharmaceutical Technology 40, 22-24, Nov. 2, 2016

Chan & McFadden, "Oncolytic Poxviruses," Ann. Rev. Virol. 1, 119-41, 2014

Chen et al., "Rapid discovery of potent siRNA-containing lipid nanoparticles enabled by controlled microfluidic formulation," J. Am. Chem. Soc. 134, 6948-51, 2012

Cherkassky et al., "Human CAR T cells with cell-intrinsic PD-1 checkpoint blockade resist tumor-mediated inhibition," J. Clin. Invest. 126, 3130-44, 2016

Chiu et al., "siRNA function in RNAi: a chemical modification analysis," RNA 2003; 9:1034-48.

Chong et al., "PD-1 blockade modulates chimeric antigen receptor (CAR)-modified T cells: refueling the CAR," Blood. 129(8), 1039-41, 2017, published on-line Dec. 28, 2016

Chowdhury et al., "Combination therapy strategies for improving PD-1 blockade efficacy: a new era in cancer immunotherapy," J. Int. Med. doi: 10.1111/joim.12708, Epub ahead of print, Oct. 26, 2017

Creative Biolabs User Manual, "TriCo-20™ Phage Display 20-mer Random Peptide Library," 14 pages, Aug. 4, 2009

Dahlman et al., "In vivo endothelial siRNA delivery using polymeric nanoparticles with low molecular weight," Nat. Nanotechnol. 9, 648-55, 2014

Dempke et al., "Second- and third-generation drugs for immuno-oncology treatment—The more the better?" Eur. J. Cancer 74, 55-72, March 2017

Desigaux et al., "Self-assembled lamellar complexes of siRNA with lipidic aminoglycoside derivatives promote efficient siRNA delivery and interference," Proc. Nat'l. Acad. Sci. (USA) 104, 16534-39, 2007

Differding, "AUNP-12—A Novel Peptide Therapeutic Targeting PD-1 Immune Checkpoint Pathway for Cancer Immunotherapy—Structure Activity Relationships & Peptide/Peptidomimetic Analogs," available at differding.com/data/AUNP_12_A_novel_peptide_therapeutic_targeting_PD_1_immune_checkpoint_pathway_for_cancer_immunotherapy.pdf, Feb. 26, 2014

Dong et al., "Lipopeptide nanoparticles for potent and selective siRNA delivery in rodents and nonhuman primates," Proc. Nat'l. Acad. Sci. (USA) 111, 3955-60, 2014

Dosta et al., "Surface charge tunability as a powerful strategy to control electrostatic interaction for high efficiency silencing, using tailored oligopeptide-modified poly(beta-amino ester)s (PBAEs)," Acta Biomater. 20, 82-93, 2015

Duraiswamy et al., "Dual Blockade of PD-1 and CTLA-4 Combined with Tumor Vaccine Effectively Restores T-Cell Rejection Function in Tumors," Cancer Res 73, 3591-603, 2013

Fenton et al., "Bioinspired alkenyl amino alcohol ionizable lipid materials for highly potent in vivo mRNA delivery," Adv. Mater. 28, 2939-43, 2016

Feridooni et al., "Noninvasive Strategies for Systemic Delivery of Therapeutic Proteins—Prospects and Challenges," Chapter 8 of Sezer, ed., Smart Drug Delivery System, available at http://www.intechopen.com/books/smart-drug-delivery-system, Feb. 10, 2016

Freeman et al., "Phase I/II trial of intravenous NDV-HUJ oncolytic virus in recurrent glioblastoma multiforme," Mol. Ther. 13, 221-28, 2006

Gao et al., "VISTA is an inhibitory immune checkpoint that is increased after ipilimumab therapy in patients with prostate cancer," Nature Med. 23, 551-55, 2017

Geevarghese et al., "Phase I/II Study of Oncolytic Herpes Simplex Virus NV1020 in Patients with Extensively Pretreated Refractory Colorectal Cancer Metastatic to the Liver," Hum. Gene Ther. 21, 1119-28, 2010

Guo et al., "Systemic delivery of therapeutic small interfering RNA using a pH-triggered amphiphilic poly-L-lysine nanocarrier to suppress prostate cancer growth in mice," Eur. J. Pharm. Sci. 45, 521-32, 2012

Harvey et al., "Efficacy of anti-ICOS agonist monoclonal antibodies in preclinical tumor models provides a rationale for clinical development as cancer immunotherapeutics," Journal for ImmunoTherapy of Cancer 3(Suppl 2), 09, 2015

He et al., "Lymphocyte-activation gene-3, an important immune checkpoint in cancer," Cancer Sci. 107, 1193-97, 2016

Howard et al., "RNA interference in vitro and in vivo using a novel chitosan/siRNA nanoparticle system," Mol. Ther. 14, 476-84, 2006

Huard et al., "Cellular expression and tissue distribution of the human LAG-3-encoded protein, an MHC class II ligand," Immunogenetics 39 (3): 213-7, 1994

Huard et al., "CD4/major histocompatibility complex class II interaction analyzed with CD4- and lymphocyte activation gene-3 (LAG-3)-Ig fusion proteins," J. Immunol. 25, 2718-21, Huseni et al., "Anti-tumor efficacy and biomarker evaluation of agonistic anti-OX40 antibodies in preclinical models," Journal for ImmunoTherapy of Cancer 2(Suppl 3), P105, 2014

Infante et al., "A phase 1b dose escalation study of the OX40 agonist MOXR0916 and the PD-L1 inhibitor atezolizumab in patients with advanced solid tumors," J Clin Oncol. 34(suppl; abstr 101), 2016

John et al., "Blockade of PD-1 immunosuppression boosts CAR T-cell therapy," OncoImmunology 2, e26286, 3 pages, 2013

Johnson et al., "A Cancer Research UK phase I study evaluating safety, tolerability, and biological effects of chimeric anti-CD40 monoclonal antibody (MAb), Chi Lob 7/4," J Clin Oncol. 28, 2507, 2010.

Johnson et al., "Clinical and Biological Effects of an Agonist Anti-CD40 Antibody: A Cancer Research UK Phase I Study," Clin Cancer Res 21, 1321-28, 2015

Judge & MacLachlan, "Overcoming the innate immune response to small interfering RNA," Hum Gene Ther. 2008; 19:111-24.

Kaczmarek et al., "Advances in the delivery of RNA therapeutics: from concept to clinical reality," Genome Medicine 2017; 9:60, 16 pages Kanasty et al., "Delivery materials for siRNA therapeutics," Nat. Mater. 12, 967-77, 2013

Kauffman et al., "Optimization of lipid nanoparticle formulations for mRNA delivery in vivo with fractional factorial and definitive screening designs," Nano Lett. 15, 7300-06, 2015

Kauffman et al., "Efficacy and immunogenicity of unmodified and pseudouridine-modified mRNA delivered systemically with lipid nanoparticles in vivo," Biomaterials. 2016; 109:78-87.

Kaufmann et al., "Chemovirotherapy of Malignant Melanoma with a Targeted and Armed Oncolytic Measles Virus," J. Invest. Dermatol. 133, 1034-42, 2013

Kavikansky & Pavlick, "Beyond Checkpoint Inhibitors: The Next Generation of Immunotherapy in Oncology," Amer. J. Hematol. Oncol. 13, 9-20, 2017

Khubchandani et al., "Dacetuzumab, a humanized mAb against CD40 for the treatment of hematological malignancies," Curr Opin Investig Drugs 10, 579-87, 2009.

Khuri et al., "A controlled trial of intratumoral ONYX-015, a selectively-replicating adenovirus, in combination with cisplatin and 5-fluorouracil in patients with recurrent head and neck cancer," Nat. Med. 6, 879-85, 2000

Kisielow et al., "Expression of lymphocyte activation gene 3 (LAG-3) on B cells is induced by T cells". European Journal of Immunology 35 (7): 2081-8, 2005

Kontermann, "Half-life extended biotherapeutics," Expert Opin. Biol. Ther. 16, 903-15, 2016.

Kozielski et al., "A bioreducible linear poly(O-amino ester) for siRNA delivery," Chem. Commun. (Camb). 49, 5319-21, 2013

Lawler et al., "Oncolytic Viruses in Cancer Treatment," JAMA Oncol. 3, 841-49, 2017 (published on-line Jul. 21, 2016)

Le Mercier et al., "VISTA Regulates the Development of Protective Antitumor Immunity," Cancer Res 2014; 74:1933-1944

Leone et al., "A2aR antagonists: Next generation checkpoint blockade for cancer immunotherapy," Computational and Structural Biotechnology Journal 13, 265-72, 2015

Leus et al., "VCAM-1 specific PEGylated SAINT-based lipoplexes deliver siRNA to activated endothelium in vivo but do not attenuate target gene expression," Int. J. Pharm. 469, 121-31, 2014

Li et al., "Discovery of peptide inhibitors targeting human programmed death 1 (PD-1) receptor," Oncotarget 7, 64967-76, Aug. 12, 2016

Li et al., "Effects of chemically modified messenger RNA on protein expression," Bioconjug Chem. 2016; 27:849-53.

Liang, "Oncorine, the World First Oncolytic Virus Medicine and its Update in China," Curr. Cancer Drug Targets 18, 171-76, 2018

Lichtenegger et al., "Targeting LAG-3 and PD-1 to Enhance T Cell Activation by Antigen-Presenting Cells," Front. Immunol. 9, 385, doi: 10.3389/fimmu.2018.00385.

Linch et al., "OX40 agonists and combination immunotherapy: putting the pedal to the metal," Frontiers in Oncology 5, 14 pages, 2015

Liu et al., "Immune-checkpoint proteins VISTA and PD-1 nonredundantly regulate murine T-cell responses," Proc. Nat'l. Acad. Sci. USA 112, 6682-87, 2015

Lorence et al., "Phase 1 clinical experience using intravenous administration of PV701, an oncolytic Newcastle disease virus," Curr. Cancer Drug Targets 7, 157-67, 2007

Lorenz et al., "Steroid and lipid conjugates of siRNAs to enhance cellular uptake and gene silencing in liver cells," Bioorganic Med. Chem. Lett. 14, 4975-77, 2004

Love et al., "Lipid-like materials for low-dose, in vivo gene silencing," Proc. Nat'l. Acad. Sci. (USA) 107, 1864-69, 2010

Lu et al., "Replicating retroviral vectors for oncolytic virotherapy of experimental hepatocellular carcinoma," Oncol. Rep. 28, 21-26, 2012

Lundstrom, "Oncolytic Alphaviruses in Cancer Immunotherapy," Vaccines 5, pages 1-17, 2017

Lynn & Langer, "Degradable poly(O-amino esters): synthesis, characterization, and self-assembly with plasmid DNA," J. Am. Chem. Soc. 122, 10761-18, 2000

Magiera-Mularz et al., "Bioactive macrocyclic inhibitors of the PD-1/PD-L1 immune checkpoint," Angewandte Chemie Int. Ed. 10.1002/anie.201707707, e-published Sep. 26, 2017

Mao et al., "Pathological α-synuclein transmission initiated by binding lymphocyte-activation gene 3," Science 353, aah3374, 2016

Maute et al., "Engineering high-affinity PD-1 variants for optimized immunotherapy and immuno-PET imaging," Proc. Natl. Acad. Sci. USA, E6506-E6514, published online Nov. 10, 2015

McDonald et al., "A measles virus vaccine strain derivative as a novel oncolytic agent against breast cancer," Breast Cancer Treat. 99, 177-84, 2006

McOmie, Protective Groups in Organic Chemistry, Plenum Press, New York, N.Y., 1973

Mediavilla-Varela et al., "A Novel Antagonist of the Immune Checkpoint Protein Adenosine A2a Receptor Restores Tumor-Infiltrating Lymphocyte Activity in the Context of the Tumor Microenvironment," Neoplasia 19, 530-36, 2017

Mellemgaard et al., "Combination immunotherapy with IDO vaccine and PD-1 inhibitors in advances HSCLC," DOI: 10.1200/JCO.2017.35.15_suppl.TPS2610 Journal of Clinical Oncology 35, no. 15_suppl—published online before print, 2017

Merrifield, "Solid phase peptide synthesis I: Synthesis of a tetrapeptide," J. Am. Chem. Soc. 85:2149-54, 1963

Messenheimer et al., "Timing of PD-1 Blockade Is Critical to Effective Combination Immunotherapy with Anti-OX40," Clin. Cancer Res. 23, DOI: 10.1158/1078-0432.CCR-16-2677 Published October 2017

Michaelson et al., "Preclinical evaluation of JTX-2011, an anti-ICOS agonist antibody,", Abstract 573, Proceedings: AACR 107th Annual Meeting 2016; Apr. 16-20, 2016; New Orleans, LA Morrissey et al., "Immunotherapy and Novel Combinations in Oncology: Current Landscape, Challenges, and Opportunities," Clinical and Translational Science 9, 89-104, 2016

Morrissey et al., "Potent and persistent in vivo anti-HBV activity of chemically modified siRNAs," Nat. Biotechnol. 23, 1002-07, 2005

Moschos et al., "Lung delivery studies using siRNA conjugated to TAT(48-60) and penetratin reveal peptide induced reduction in gene expression and induction of innate immunity," Bioconjug. Chem. 18, 1450-59, 2007

Nair et al., "Multivalent N-acetylgalactosamine-conjugated siRNA localizes in hepatocytes and elicits robust RNAi-mediated gene silencing," J. Am. Chem. Soc. 136, 16958-61, 2014

Neurath et al., eds., The Proteins, Vol. II, 3d ed., pp. 105-237, Academic Press, New York, NY (1976)

Nishina et al., "Efficient in vivo delivery of siRNA to the liver by conjugation of alphatocopherol.," Mol. Ther. 16, 734-40, 2008

Ott et al., "Combination immunotherapy: a road map," J. ImmunoTherapy of Cancer 5, 16, 2017

Pack et al., "Design and development of polymers for gene delivery," Nat. Rev. Drug discov. 4, 581-93, 2005

Patel et al., "Recent Advances in Protein and Peptide Drug Delivery: A Special Emphasis on Polymeric Nanoparticles," Protein. Pept. Lett. 21, 1102-20, 2014

Patil et al., "Targeting Immune Cell Checkpoints During Sepsis," Int. J. Mol. Sci. 18, 2413, 2017.

Penchala et al., "A biomimetic approach for enhancing the in vivo half-life of peptides," Nat. Chem. Biol. 11, 793-98, 2015

Phuangsab et al., "Newcastle disease virus therapy of human tumor xenografts: antitumor effects of local or systemic administration," Cancer Lett. 172, 27-36, 2001

Prakash et al., "Positional effect of chemical modifications on short interference RNA activity in mammalian cells," J Med Chem. 2005; 48:4247-53

Pratt & MacRae, "The RNA-induced silencing complex: a versatile gene-silencing machine," J Biol Chem. 2009; 284:17897-901

Rehman et al., "Mechanism of polyplex- and lipoplex mediated delivery of nucleic acids: real-time visualization of transient membrane destabilization without endosomal lysis," ACS Nano. 7, 3767-77, 2013

Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. 153, 1162-65, 2017

Rodríguez et al., "Design and implementation of a high yield production system for recombinant expression of peptides," Microbial Cell Factories 13, 65, 10 pages, 2014

Rudin et al., "Phase I clinical study of Seneca Valley Virus (SVV-001), a replication-competent picornavirus, in advanced solid tumors with neuroendocrine features," Clin. Cancer Res. 17, 888-95, 2011

Sahin et al., "mRNA-based therapeutics-developing a new class of drugs," Nat Rev Drug Discov. 2014; 13:759-80

Sakuishi et al., "Targeting Tim-3 and PD-1 pathways to reverse T cell exhaustion and restore anti-tumor immunity," J. Exp. Med. 20, 2187-94, 2010

Schaer et al., "Modulation of GITR for cancer immunotherapy," Curr Opin Immunol. 24, 217-24, 2012

Schroeder et al., "Lipid-based nanotherapeutics for siRNA delivery," J. Int. Med. 267, 9-21, 2010

Sharma & Allison, "Immune Checkpoint Targeting in Cancer Therapy: Toward Combination Strategies with Curative Potential," Cell 161, 205-14, 2015

Shindo et al., "Combination Immunotherapy with 4-1BB Activation and PD-1 Blockade Enhances Antitumor Efficacy in a Mouse Model of Subcutaneous Tumor," Anticancer Res. 35, 129-36, 2015

Shrimali et al., "Concurrent PD-1 Blockade Negates the Effects of OX40 Agonist Antibody in Combination Immunotherapy through Inducing T-cell Apoptosis," Cancer Immunol Res 5(9), pages OF1-12, Aug. 28, 2017

Skalniak et al., "Small-molecule inhibitors of PD-1/PD-L1 immune checkpoint alleviate the PD-L1-induced exhaustion of T-cells," Oncotarget, Advance Publications, Aug. 7, 2017, 15 pages Smith, "Pigmented skin lesions lightened during melanoma immunotherapy," http://www.mdedge.com/edernatology-news/article/132598/melanoma/pigmented-skin-lesions-lightened-during-melanoma, Mar. 2, 2017

Soutschek et al., "Therapeutic silencing of an endogenous gene by systemic administration of modified siRNAs," Nature. 2004; 432:173-78

Spodzieja et al., "Design of short peptides to block BTLA/HVEM interactions for promoting anticancer T-cell responses," PLoS ONE 12(6): e0179201, 17 pages, 2017

Stojdl et al., "Exploiting tumor-specific defects in the interferon pathway with a previously unknown oncolytic virus," Nat. Med. 6, 821-25, 2000

Stojdl et al., "VSV strains with defects in their ability to shutdown innate immunity are potent systemic anti-cancer agents," Cancer Cell 4, 263-75, 2003

Stuart & Young, Solid Phase Peptide Synthesis, Pierce Chemical Company, Rockford, IL, Tigue et al., "MEDI1873, a potent, stabilized hexameric agonist of human GITR with regulatory T-cell targeting potential," ONCOIMMUNOLOGY 6(3), e1280645 (14 pages), Feb. 3, 2017

Triebel et al., "LAG3, a novel lymphocyte activation gene closely related to CD4," J. Exp. Med. 171, 1393-405, 1990

Tsutsumi et al., "Evaluation of polyamidoamine dendrimer/alpha-cyclodextrin conjugate (generation 3, G3) as a novel carrier for small interfering RNA (siRNA)," J. Control. Release 119, 349-59, 2007

Tuck, "Development of Small Molecule Checkpoint Inhibitors," Immune Checkpoint Inhibitors Symposium, 28 pages, Mar. 14-16, 2017

Tzeng et al., "Cystamine-terminated poly(beta-amino ester)s for siRNA delivery to human mesenchymal stem cells and enhancement of osteogenic differentiation," Biomaterials 33, 8142-51, 2012

Tzeng et al., "PD-1 blockage reverses immune dysfunction and hepatitis B viral persistence in a mouse animal model," PLoS One 7(6):e39179, 2012

Van Dessel et al., "Potent and tumor specific: arming bacteria with therapeutic proteins," Ther. Deliv. 6, 385-99, 2015

Vonderheide and Glennie, "Agonistic CD40 antibodies and cancer therapy," Clin. Cancer Res. 19, 1035-43, 2013

Vonderheide et al., "Clinical activity and immune modulation in cancer patients treated with CP-870,893, a novel CD40 agonist monoclonal antibody," J Clin Oncol. 25, 876-83, 2007

Wang et al., "Anaplastic lymphoma kinase (ALK) inhibitors: a review of design and discovery," Med. Chem. Commun. 5, 1266-79, 2014

Wang et al., "VISTA, a novel mouse Ig superfamily ligand that negatively regulates T cell responses," J. Exp. Med. 208, 577-92, 2011

Wang et al., "Fibrinogen-like Protein 1 is a Major Immune Inhibitory Ligand of LAG-3," Cell 176, 334-47, 2019

Wittrup & Lieberman, "Knocking down disease: a progress report on siRNA therapeutics," Nat Rev Genet. 2015; 16:543-52

Won et al., "Missing pieces in understanding the intracellular trafficking of polycation/DNA complexes," J. Control. Release 139, 88-93, 2009

Workman et al., "LAG-3 regulates plasmacytoid dendritic cell homeostasis," Journal of Immunology 182 (4): 1885-91, 2009

Xia et al., "Antibody-mediated targeting of siRNA via the human insulin receptor using avidin-biotin technology.," Mol. Pharm. 6, 747-51, 2009

Yang et al., "Oral vaccination with *Salmonella* simultaneously expressing *Yersinia pestis* F1 and V antigens protects against bubonic and pneumonic plague," J Immunol. 178, 1059-67, 2007

Ye et al., "T-cell exhaustion in chronic hepatitis B infection: current knowledge and clinical significance," Cell Death Dis. 19, e1694, 2015

Young et al., "Co-inhibition of CD73 and A2AR Adenosine Signaling Improves Anti-tumor Immune Responses," Cancer Cell 30, 391-403, 2016

Yu et al., "Disposition and pharmacology of a GalNAc3-conjugated ASO targeting human lipoprotein(a) in mice," Mol. Ther. Nucleic Acids 5, e317, 2016

Zarganes-Tzitzikas et al., "Inhibitors of programmed cell death 1 (PD-1): a patent review," Expert Opinion on Therapeutic Patents 26, 973-77, published on-line Jul. 6, 2016

Zhan et al., "From monoclonal antibodies to small molecules: the development of inhibitors targeting the PD-1/PD-L1 pathway," Drug Discovery Today 21, 1027-36, June 2016

Zorzi et al., "Acylated heptapeptide binds albumin with high affinity and application as tag furnishes long-acting peptides," Nature Communications 8, 16092, 2017

The invention claimed is:

1. A nucleic acid encoding a peptide comprising an amino acid sequence selected from the group consisting of SEQ ID NOS: 1, 2, 3, 4, 5, 6, and 7.

2. The nucleic acid of claim 1, wherein the peptide consists essentially of the amino acid sequence.

3. The nucleic acid of claim 2, wherein the peptide consists of the amino acid sequence.

4. The nucleic acid of claim 1, which is an expression construct.

5. The nucleic acid of claim 1, wherein the nucleic acid is selected from the group consisting of DNA, cDNA, PNA, and RNA.

6. A host cell comprising the nucleic acid of claim 1.

7. The nucleic acid of claim 5, wherein the nucleic acid is RNA.

8. The nucleic acid of claim 7, wherein the RNA comprises a modification selected from the group consisting of (i) modification of a ribose sugar, (ii) modification of a phosphate linkage, and (iii) modification of a base.

9. The nucleic acid of claim 8, wherein the modification is selected from the group consisting of a ribo-difluorotoluyl-modified nucleotide, a 4'-thio modified RNA, a boranophosphate linkage, a phosphorothioate linkage, a 2'-O-methyl (2'-OMe) sugar substitution, a 2'-fluoro (2'-F), a 2'-O-methoxyethyl (2'-MOe) sugar substitution, and a locked nucleic acid (LNA).

10. The nucleic acid of claim 7, wherein the RNA comprises L-RNA.

11. The host cell of claim 6, wherein the host cell is a CAR-T cell that expresses the nucleic acid of claim 1.

12. An oncolytic virus comprising a nucleic acid encoding a peptide comprising an amino acid sequence selected from the group consisting of SEQ ID NOS: 1, 2, 3, 4, 5, 6, and 7.

* * * * *